(12) United States Patent
Carol et al.

(10) Patent No.: US 9,409,040 B2
(45) Date of Patent: *Aug. 9, 2016

(54) DELIVERY SYSTEM FOR RADIATION THERAPY

(71) Applicant: Triple Ring Technologies, Inc., Newark, CA (US)

(72) Inventors: Mark Philip Carol, Burlingame, CA (US); Joseph Anthony Heanue, Oakland, CA (US)

(73) Assignee: Triple Ring Technologies, Inc., Newark, CA (US)

( * ) Notice: Subject to any disclaimer, the term of this patent is extended or adjusted under 35 U.S.C. 154(b) by 273 days.

This patent is subject to a terminal disclaimer.

(21) Appl. No.: 14/170,478

(22) Filed: Jan. 31, 2014

(65) Prior Publication Data

US 2014/0205067 A1    Jul. 24, 2014

Related U.S. Application Data

(60) Continuation of application No. 13/279,208, filed on Oct. 21, 2011, now Pat. No. 8,644,452, which is a division of application No. 12/251,298, filed on Oct. 14, 2008, now Pat. No. 8,050,384, which is a continuation of application No. 11/149,565, filed on Jun. 9, 2005, now abandoned.

(60) Provisional application No. 60/578,721, filed on Jun. 10, 2004, provisional application No. 60/578,720, filed on Jun. 10, 2004.

(51) Int. Cl.
*A61N 5/10* (2006.01)

(52) U.S. Cl.
CPC .............. *A61N 5/1031* (2013.01); *A61N 5/10* (2013.01); *A61N 5/1037* (2013.01); *A61N 5/1039* (2013.01); *A61N 5/1049* (2013.01); *A61N 5/1084* (2013.01); *A61N 2005/1059* (2013.01); *A61N 2005/1091* (2013.01); *A61N 2005/1098* (2013.01)

(58) Field of Classification Search
CPC ............................................. A61N 2005/1091
See application file for complete search history.

(56) References Cited

U.S. PATENT DOCUMENTS

| | | | |
|---|---|---|---|
| 6,097,833 A * | 8/2000 | Lobregt et al. | 382/130 |
| 2002/0051513 A1 * | 5/2002 | Pugachev et al. | 378/65 |
| 2002/0065461 A1 * | 5/2002 | Cosman | 600/426 |

* cited by examiner

*Primary Examiner* — Hoon Song

(57) ABSTRACT

A device is used to precisely deliver the treatment plan created by an automatic planning system by positioning a single low energy radiation source, or a plurality of low energy sources connected to each other, in a predetermined parallel, planar, or similar geometry, each source equipped with blocking and attenuation mechanisms, thereby delivering a plurality of parallel overlapping beams indexed on a millimeter or submillimeter grid such that a concentration of dose is achieved at a variable depth in tissue relative to the dose where the radiation first enters the tissue. A plurality of overlapping beams indexed on a millimeter or submillimeter grid can converge on a target volume loaded with gold nanoparticles to deliver a tumorcidal dose of radiation in as little as a single session to tumor cells but not to normal cells or to deliver serial radiosurgical treatments.

20 Claims, 25 Drawing Sheets

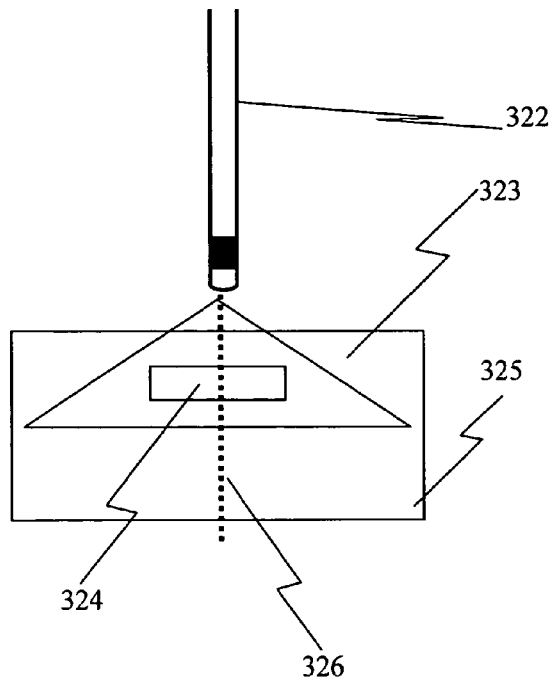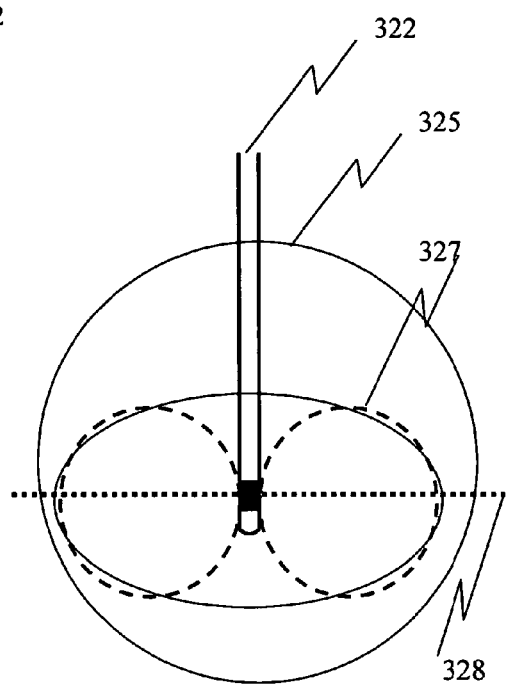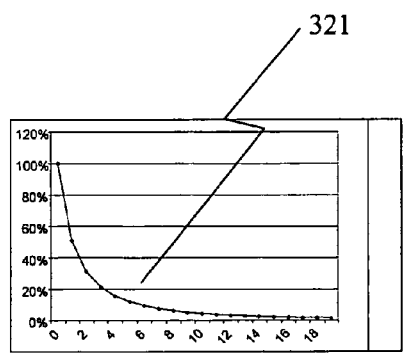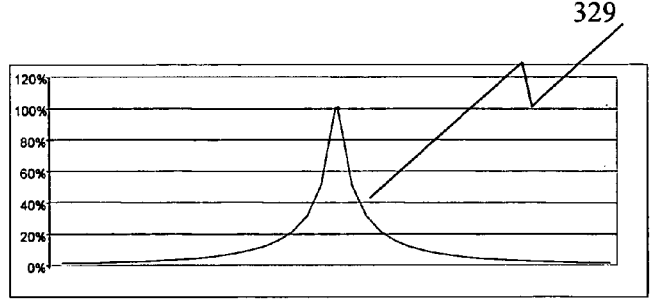
FIG 1A
FIG 1B
FIG 1C
FIG 1D

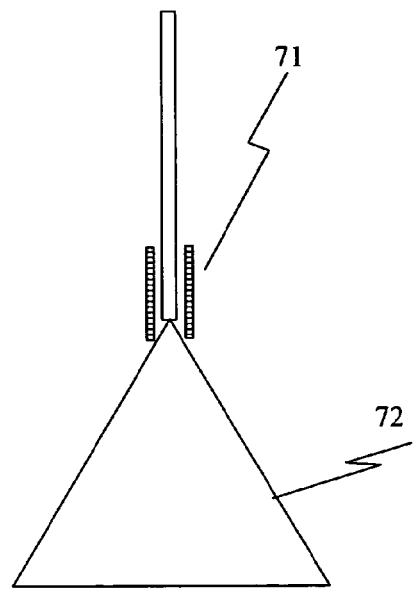
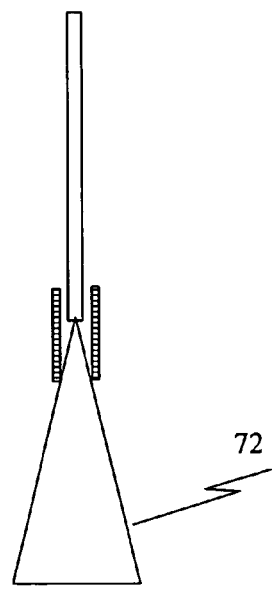
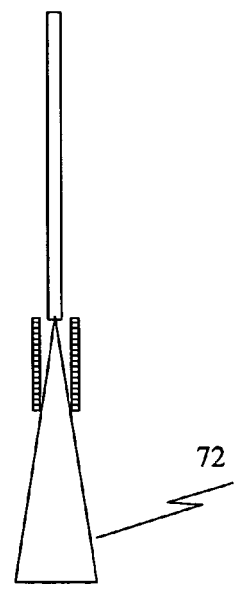
FIG 7A        FIG 7B        FIG 7C
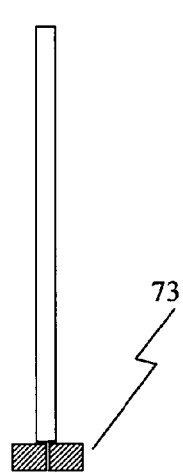
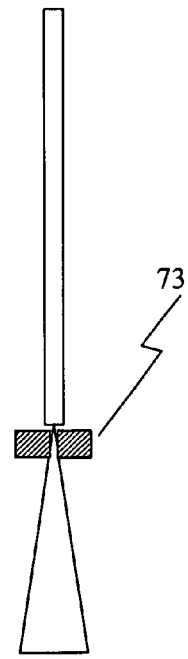
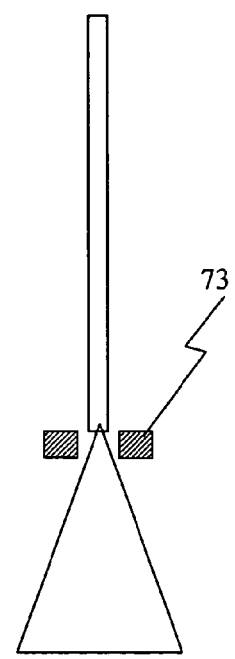
FIG 7D        FIG 7E        FIG 7F

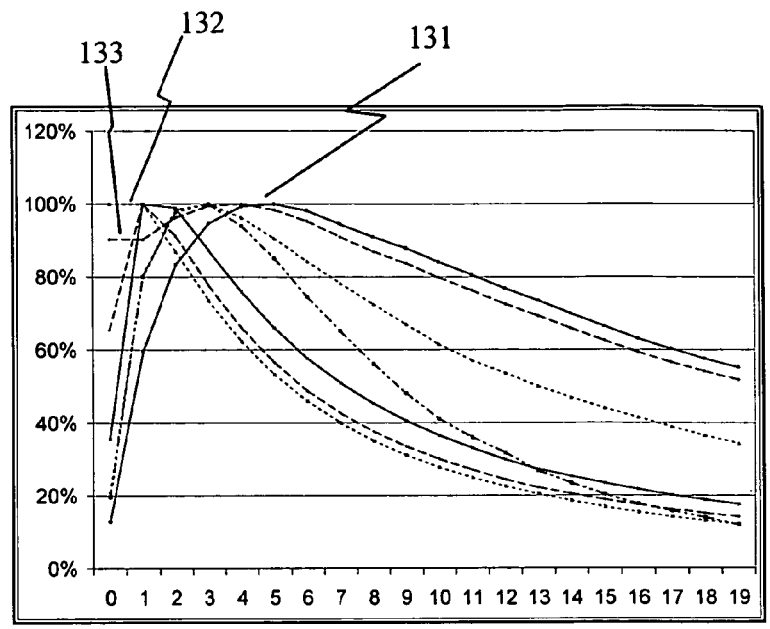
FIG 13
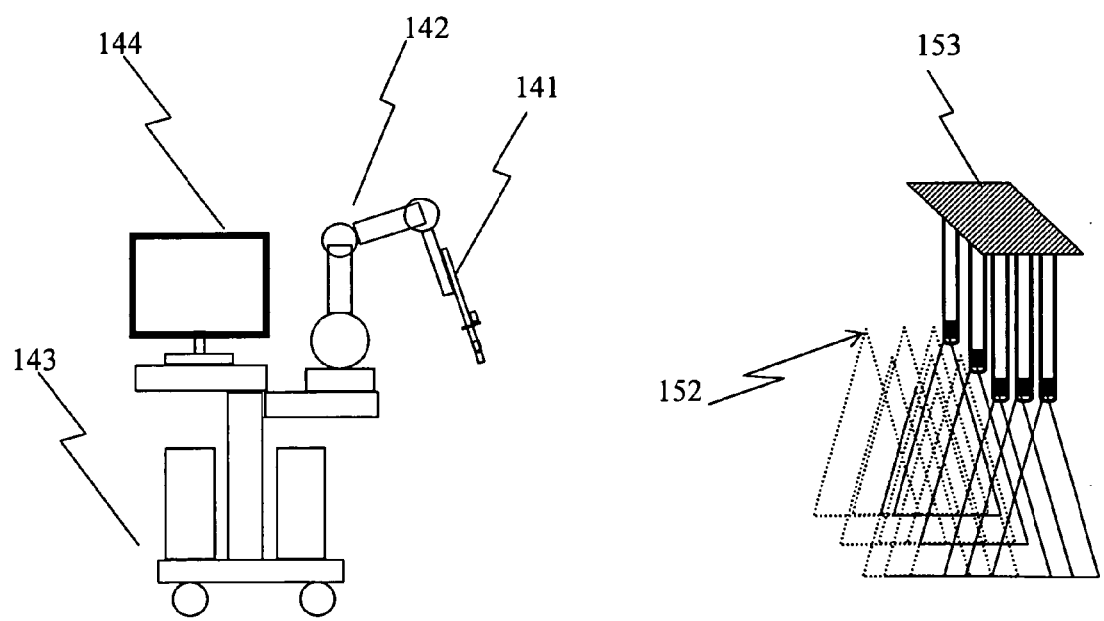
FIG 14
FIG 15

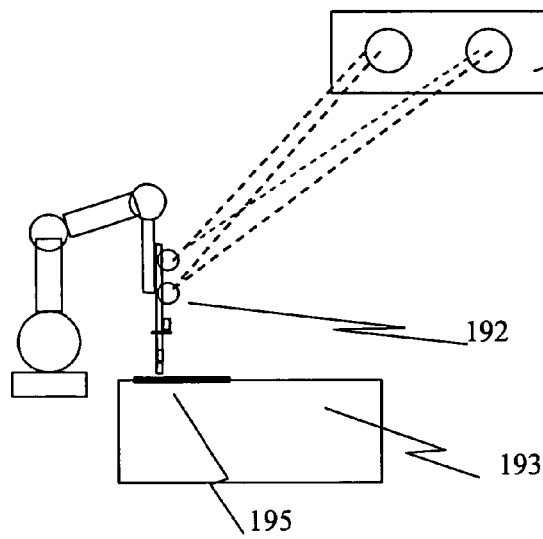
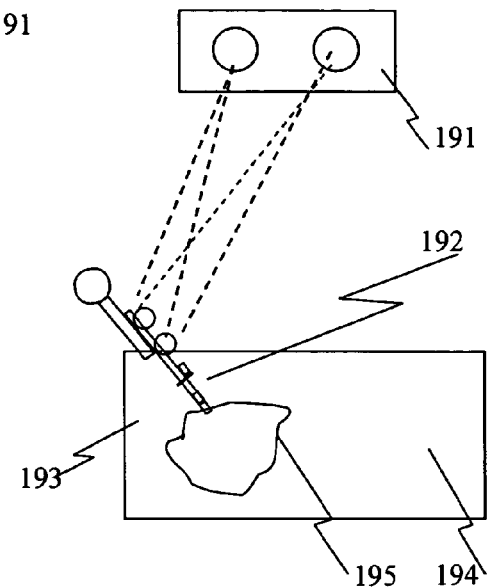
FIG 19A  FIG 19B
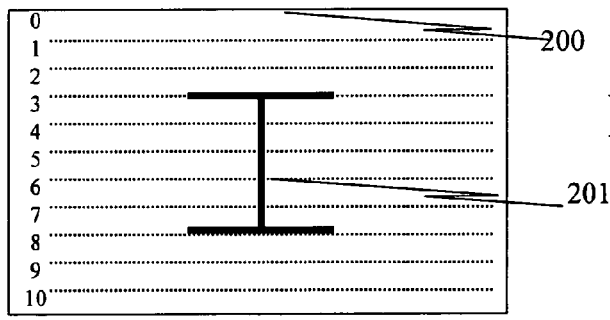
FIG 20A
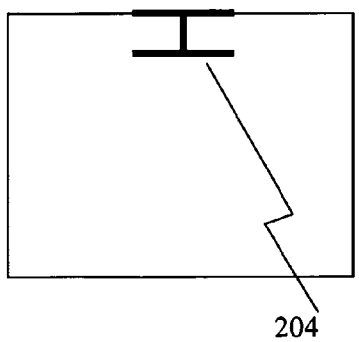
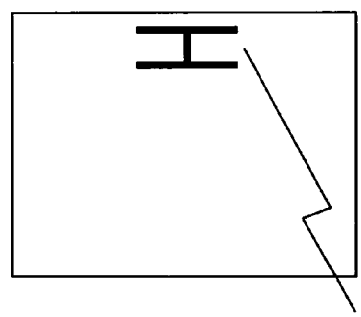
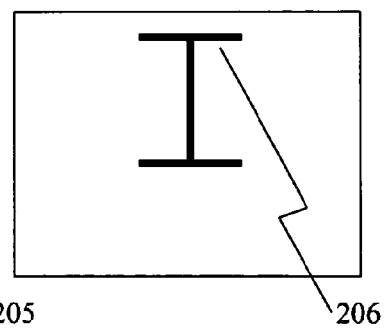
FIG 20B  FIG 20C  FIG 20D

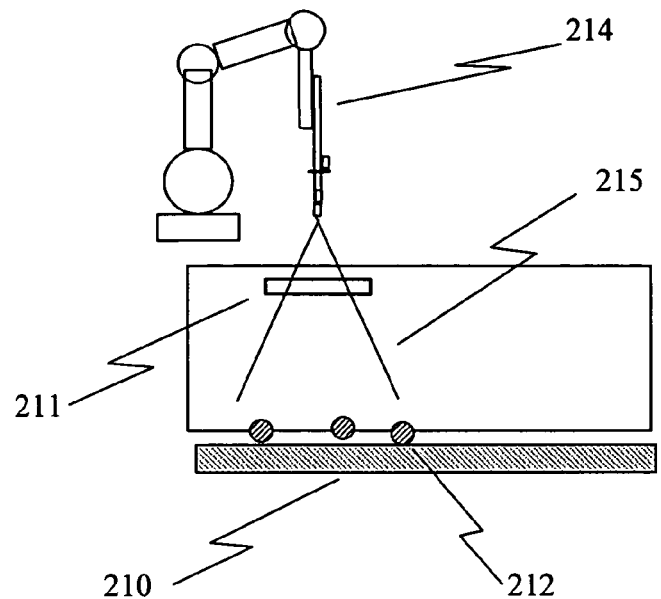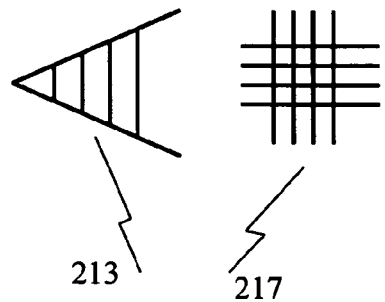
FIG 21A  FIG 21B
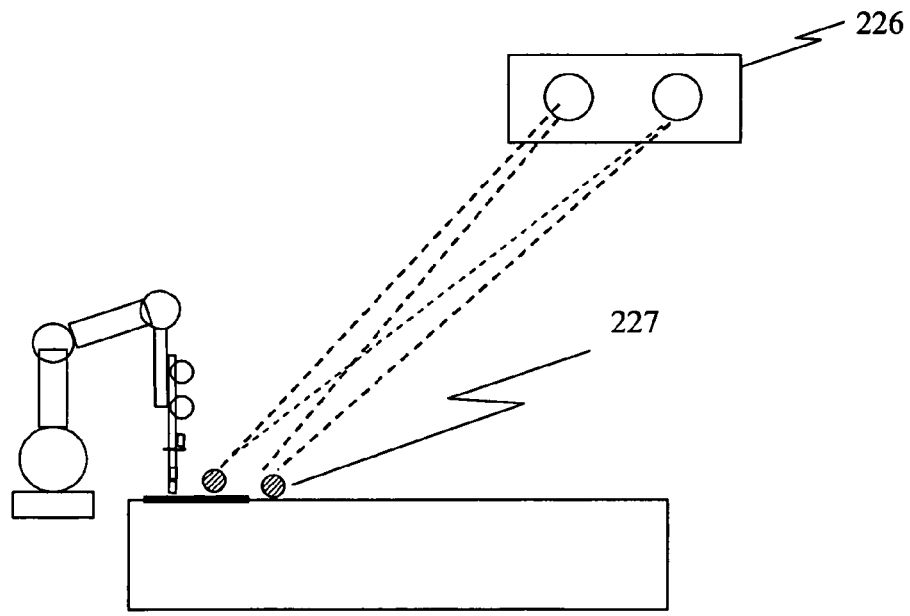
FIG 22

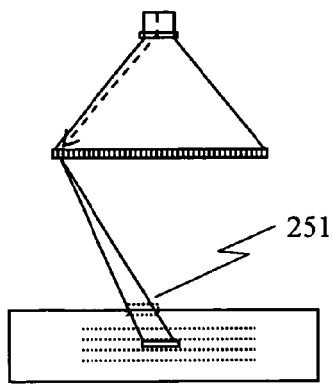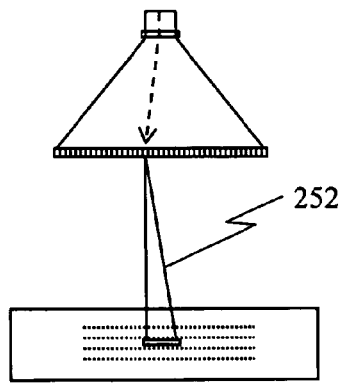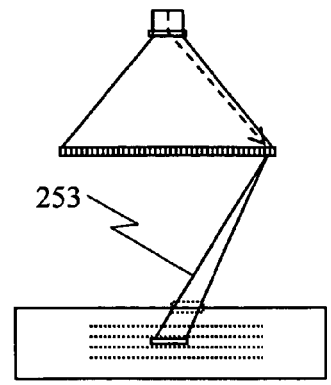
FIG 25A     FIG 25B     FIG 25C
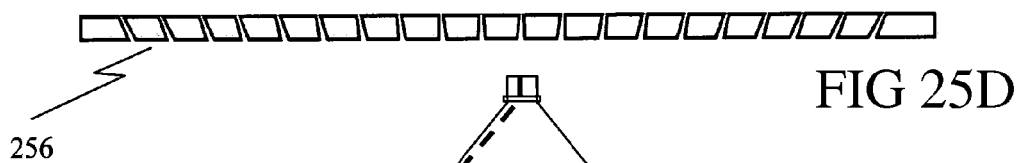
FIG 25D
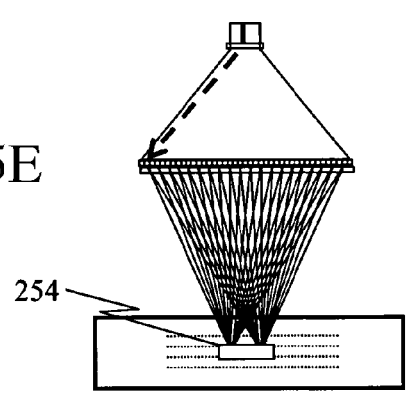
FIG 25E
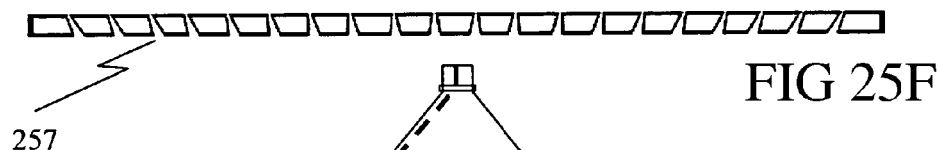
FIG 25F
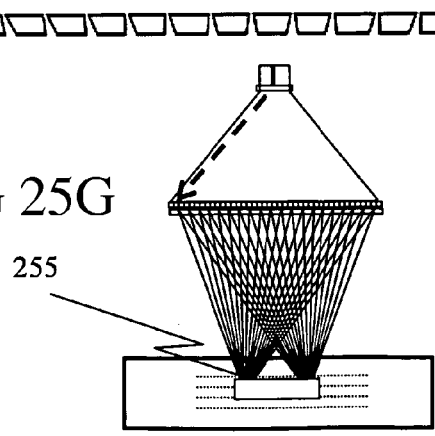
FIG 25G

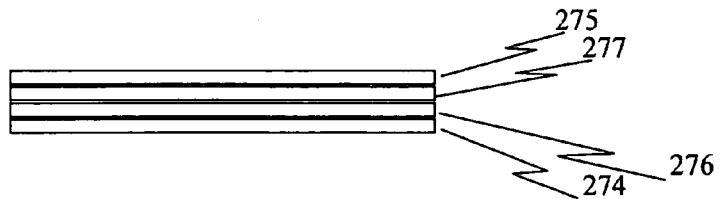
FIG 27A
FIG 27B
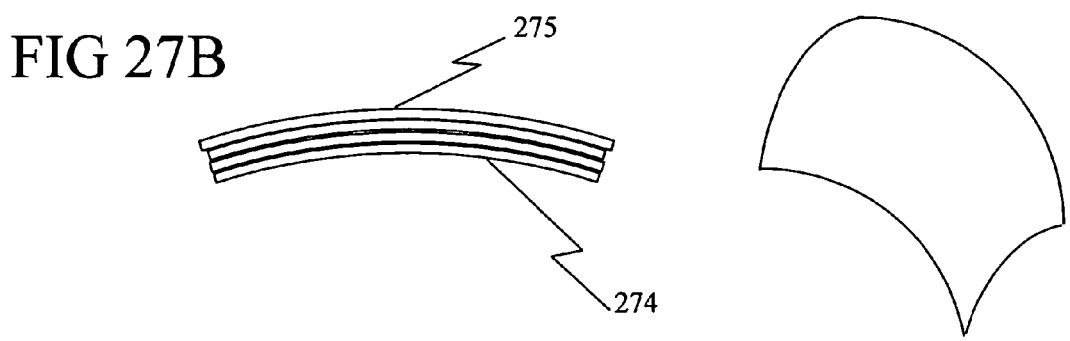
FIG 27C
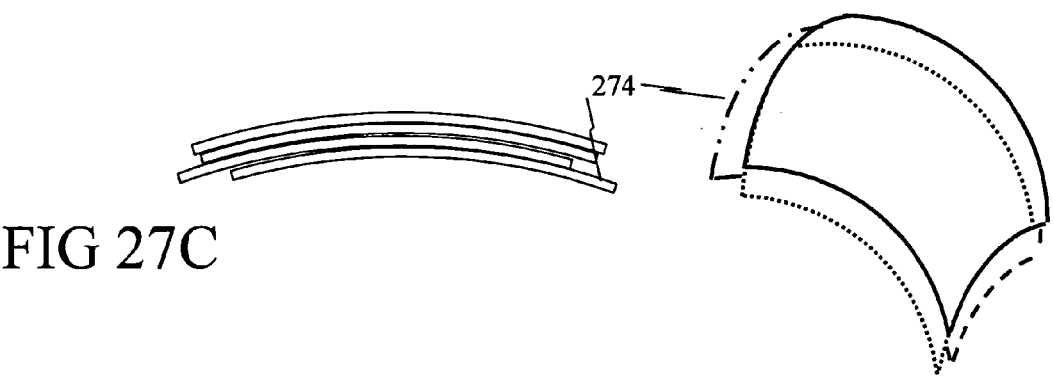
FIG 27D
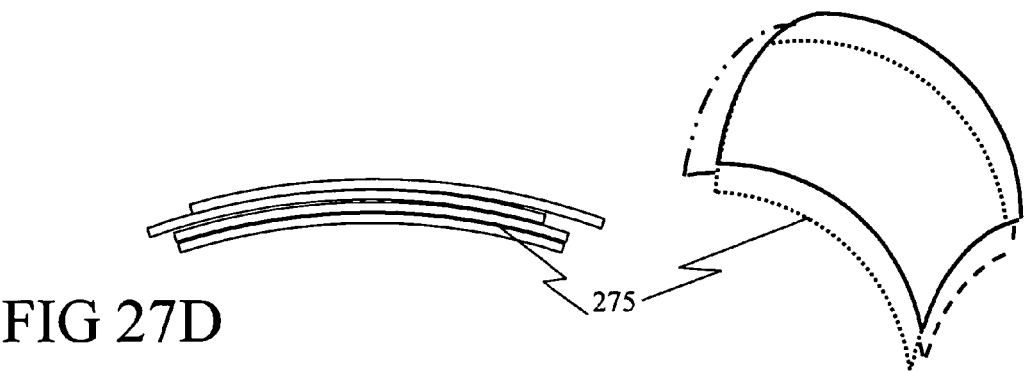

DELIVERY SYSTEM FOR RADIATION THERAPY

CROSS-REFERENCE TO RELATED APPLICATIONS

This application is a continuation application claiming priority from the U.S. non-provisional patent application Ser. No. 13/279,208, entitled "DELIVERY SYSTEM FOR RADIATION THERAPY," with filing date Oct. 21, 2011, which is a divisional application claiming priority from U.S. patent application Ser. No. 12/251,298, now U.S. Pat. No. 8,050,384, entitled "DELIVERY SYSTEM FOR RADIATION THERAPY," with filing date Oct. 14, 2008, which is a continuation of U.S. patent application Ser. No. 11/149,565, entitled "Kilovoltage delivery system for radiation therapy," with filing date Jun. 9, 2005, all of which are incorporated herein by reference. U.S. patent application Ser. No. 11/149,565 claims priority to U.S. provisional patent application Ser. No. 60/578,720, with filing date Jun. 10, 2004 and U.S. provisional patent application Ser. No. 60/578,721, with filing date Jun. 10, 2004.

STATEMENT REGARDING FEDERALLY SPONSORED RESEARCH OR DEVELOPMENT

None

BACKGROUND

1. Field of the Invention

This invention relates to the use of low energy radiation as a treatment for cancer and other conditions.

2. Description of Prior Art

Radiation Therapy for Targets in Proximity to Treatment Device

Radiation therapy has been a very successful and well-utilized means for controlling and sometimes even curing cancer. Most commonly delivered in an outpatient setting over several weeks, RT is delivered usually using machines capable of delivering high energy photons (megavoltage, MV) in a very controlled manner using ancillary devices such as multileaf collimators, intensity modulating delivery paradigms, and portal imaging systems for monitoring treatment delivery. Since the high energy of the x-rays generated by these machines can penetrate very deeply, these machines can be used to treat tumors occurring deep inside the body.

Superficial Cancers

Unfortunately, sophisticated MV delivery systems may not be able to treat superficial cancers such as those of the skin or nonmalignant lesions of the skin such as keloids. This inability to treat superficial lesions is due to the nature of the differential dose deposited at depth with MV energy x-rays; these x-rays deliver a much lower dose within mm to cm of the surface than they do at depth due to the buildup of dose from scattered electrons as the beam passes through tissue. Thus it is difficult to deliver enough dose near the skin surface without overdosing tissue lying under the skin.

MV delivery systems also may not be applicable for use in the treatment of tumors that receive radiation therapy at the time of surgery. Called intraoperative radiation therapy (IORT), this special technique permits the application of a high dose of radiation during surgery. The possibility of manually moving healthy organs situated in between of the radiation beam and the target out of the beam path reduces the toxicity of the therapy. In addition, the possibility of directly visualizing the area of intervention improves the degree of precision inherent in the administration of the radiation dose. IORT offers several advantages: it may eliminate post-surgery residual tumor; offer an intensification of the antitumoral effect of the radiotherapy in that it permits the administration of a higher dose of radiation than would otherwise be possible with external beam irradiation; reduce the time lapse between the surgical removal and the irradiation, a period of time during which residual cellular clones can grow.

Intraoperative Radiation Therapy

IORT ideally should be given in the operating room ("OR"). However, conventional MV radiation equipment is very heavy and large and requires thick concrete walls to contain the stray radiation produced by the equipment. This has restricted OR-based IORT to a handful of hospitals that have been able to absorb the high costs associated with the equipment and the construction of large shielded room in the OR. Most other hospitals throughout the world that conduct IORT do so by performing the operation in the OR and then transporting the patient, still under anesthesia and with the surgical site open, to the radiation facility for the radiation portion of their treatment. After the radiation treatment is completed, the patient is then transported back to the OR for the completion of the operation. This method of IORT involves very complex logistics, increases patient risk, severely limits the number of patients that can be treated, and reduces the potential efficacy of the treatment.

Other Approaches

MV devices have a range of other problems as well. Ranging in price from $1 M to in excess of $4 M depending on features, external beam megavoltage delivery devices are very complicated to build and are quite time consuming when it comes to creating a plan for delivering the treatment and in actually delivering the treatment. They require very controlled environments (temperature, power, and humidity) in which to operate and must be installed in specially designed and shielded rooms in order to protect personnel from stray radiation. They require constant and expensive maintenance and monitoring, suffer from significant downtime, and only can be used by highly trained personnel working in dedicated departments.

As a result, a variety of techniques have been developed or are being explored to improve the delivery of a tumorcidal dose of radiation to superficial lesions either in an outpatient or intraoperative setting. Electrons, rather than x-rays, can be used for superficial skin treatments. Generated by the same megavoltage machines as x-rays, electrons pass less deeply into tissue and therefore have been used to treat superficial lesions. Electrons also can be used to deliver radiation to a tumor bed while the patient is undergoing surgery. Recently mobile IORT treatment units have been developed that can be used directly in an OR. These units are electron-based, and therefore require minimal shielding. Because the treatment is delivered in the OR the biological effectiveness of the treatment should be improved through their use.

Their major disadvantages are that they are not as easy to characterize and plan for as are photons and they add cost to the price of the already expensive MV device (which is used to generate them). They also have limitations when used to treat lesions that are directly under the skin surface. In terms of IORT, although much more mobile and user friendly than their predecessors, mobile electron units still weigh close to one ton and are large and ungainly, making it difficult to move them around in an OR and bring them in opposition to the treatment site, and are expensive in terms of user and patient time. They also are relatively imprecise in terms of their ability to treat irregularly shaped tumors and are quite time-consuming to plan for and use.

Low Energy Therapeutic Radiation

Kilovoltage x-ray units and orthovoltage devices also have been used to treat superficial tumors and other abnormalities. Whereas MV devices deliver x-rays with an energy of 1 MV to 20 or more MV, superficial machines deliver kilovoltage (KV) x-rays with an energy of about 20-80 KV (orthovoltage machines operate at 150-400 KV). These devices are low cost, easy to build, and can be made very compact (with a tube as small as several mm in diameter). In addition, they can be used easily and cheaply to image the patient at the same time the patient is being treated, allowing localization of the target and monitoring of the impact of treatment. Because they are low energy they require very little in the way of user and patient shielding, making them able to be installed in almost any environment, increasing safety and reducing significantly the cost of building a treatment facility.

The major downside to low energy x-rays that has limited severely their use in modern day cancer treatment is that they have very poor penetration in tissue. Superficial machines are designed to treat to a depth of 1-3 mm and orthovoltage machines to a depth of 3-20 mm (both ranges depend on energy). They have also a surface dose that is as much as a hundred times more than the dose at depth resulting in the potential for severe skin reactions when treating deeper lesions. As a result therapeutic low energy x-rays delivered by traditional means are very limited in their applications.

One approach that has been explored for improving this situation is to deliver the low energy x-rays in a rotational fashion such as with a CT scanner. When an x-ray source is rotated about the target with the target at the center of rotation, different portions of the skin are subjected to the x-ray beam as it is directed to the isocenter. This keeps the overall skin dosage at any one location relatively low compared to the concentrated dose at the target. This approach has been explored for use in radiosurgical treatments but is severely limited for superficial applications. Rotational treatments are only as good as the extent of the angle of rotation—the greater the solid angle of rotation, the greater the range of delivery positions of the x-rays relative to the position of the target, thus the greater the dose at depth and the lower the skin dose. The best results are achieved when the x-rays can be rotated through as many as 360 degrees or more. Unfortunately, because the depth of penetration of KV x-rays is so poor, there are limited geometries that can be used through which to rotate the beam for superficial target locations, resulting in only several degrees of rotation and therefore very little increase in dose at depth or lowering of skin dose.

Another approach that has been used to improve the effectiveness of KV x-rays involves the use of optically focused beams. A series of mirrors are used to redirect KV x-rays such that they are concentrated in a spot at depth in tissue. By so doing, the dose to skin is reduced, the depth at which dose is possible is increased, and the rate at which dose is deposited at depth is increased. Perhaps as important for very small lesions, the dose falloff can be very sharp at the edges of the treatment field. Effective at achieving the desired goals, this approach requires the construction of a complex focusing system. Although such can be designed as an add-on device to an existing orthovoltage systems, it increases the cost very significantly and prices it out of the reach of practicing physicians. It also is quite inefficient, as the reduction in skin dose and the increase in treatment depth and dose rate at depth are achieved by concentrating the x-ray beam at a very small spot, the gains being proportional to the decrease in spot size. Thus larger lesions would need to be treated by scanning the spot across the target, achieved either by moving the patient under the delivery device or by mounting the delivery device in such a manner that the spot can be scanned over an immobilized patient; either approach adds considerably to the cost of the overall system. When this is performed, the approach also looses much of its sharp dose fall-off at the beam edges. In addition, it is not meant to treat superficial lesions; the process of focusing the dose would result in a potential increase in skin dose if the treatment were delivered to a superficial location. Finally, this system, like all other radiation therapy systems, requires extensive preplanning and control over patient position in order to insure that the correct dose is delivered to the correct location within the patient.

Devices for delivering low energy x-rays also can be inserted directly into the region in question in order to deliver a turmorcidal dose, or can be delivered to a deep location by a needle that is delivered to the tumor by percutaneous puncture or by passage through a lumen or hollow viscus. This approach also is plagued by the problems inherent to date in using low energy x-rays, namely the dose where the x-ray beam first enters tissue at the center of the volume being treated is very much greater than the dose in the rest of volume being treated. Attempts have been made to mitigate this problem by using multiple electronic x-ray sources or multiple positions of a single x-ray source but this increases the invasiveness of the procedure.

Radioactive isotopes also can be used to treat deep volumes and can be used as well to treat superficial lesions and to treat the cavity exposed at the time of surgical resection. This can be done by shielding the isotope to control the direction in which the radiation is delivered and then passing the isotope through channels contained in a matrix that is laid on the skin surface or in the resection cavity. However, the problem with radioactive isotopes is the same as with KV or low energy radiation—the dose is very much higher at the point(s) where the dose enters the tissue than at any other place. This makes it very difficult to deliver a uniform dose to a thickness of tissue or to deliver a dose at depth that is greater than the dose delivered to the tissue surface.

Target Identification

There also are problems associated with defining the region to be treated and to making sure that the correct region is treated. Typically, patients are imaged with CT or MR or ultrasound in order to identify the target volume. The images generated from these procedures are usually transferred into a treatment planning system where the target volume is outlined. It is then required that the patient position at the time of treatment be registered to the patient position at the time of imaging so that the treatment plan, created for a target volume spatially defined based on the patient position at the time of imaging, is correct based on the patient position at the time of treatment. This is a process that, because of its complexity and the difficulty in positioning patients, is prone to error.

Need

Thus what is needed is a low cost system using low energy radiation that can treat regions of tissue of variable depth in a range of locations in a patient, such as regions on or below the surface of tissue, in a cavity and the underlying region created following a surgical resection, on or below the surface of an internal cavity, hollow viscus, or lumen, or deep in tissue adjacent to an inserted probe or conduit or catheter, by delivering a dose at depth that is equal to or greater than the dose at the point of radiation emission without the need to preimage the patient or preplan the treatment and in an automatic fashion such that the practitioner is released from the requirement of guiding and delivering the treatment in a manual fashion, thereby improving accuracy and outcome, increasing the access of patients to such treatment, and decreasing the risk to the user.

Targets Deep to the Delivery Device
The Need

In addition to the need for new apparatus and methods for treating superficial lesions or lesions in close proximity to the radiation delivery device there also is a need for new apparatus and methods when treating tumors that are deep to the tissue surface or that are not accessible by a needle or that are disseminated diffusely in tissue. The theoretical goal of any intervention for cancer, especially for such tumors, is to eliminate malignant cells without effecting normal tissue. This is only theoretical because all known therapies have side effects that limit their usefulness. This is especially the case for radiation therapy.

It is well known that any cancer cell can be killed if subjected to a high enough single dose of radiation. Such single session treatments also are attractive to patients because if the limited amount of time they need to spend receiving treatment. A specialized radiation therapy delivery technique called radiosurgery has been developed so that the dose that can be delivered to deep targets can be increased such that certain targets can in fact be treated in a single session. This is accomplished by moving the x-ray source patient; a series of exposures in which the beam is aimed at the tumor from different directions, including a series of rotational arcs, will keep a high dose on the tumor while spreading dose to healthy tissue over a much larger volume, significantly reducing dose to the healthy tissue.

However, because this single dose of radiation also will kill all surrounding and interwoven normal cells within the treatment field, it is limited currently in the types of tumors it can treat. Also, its cost, believed to cost in excess of $5 M for equipment, room, and specialized supporting infrastructure, limits its availability. As a result of the clinical and limited access issues, most radiation therapy is delivered using a large number of small doses (fractions). This approach is less effective (in terms of malignant cell kill) and takes more time (multiple treatments over weeks versus a single treatment on a single day) but is safer (in terms of normal tissue function) because normal cells receive less dose per treatment. Since normal cells effectively are marginally less affected by radiation than malignant cells, the cumulative effect of the radiation over time is to destroy cancer cells while allowing normal cells to continue to function.

Unfortunately, the marginal difference between the effect of radiation on malignant cells and normal cells is not great enough to allow radiation to be delivered to both regions indiscriminately, even with fractionation without incurring serious side effects. As a result much time and effort has gone into designing equipment and creating delivery techniques that allow the greatest possible physical separation between normal and malignant cells so that the normal cells will receive less radiation than the malignant cells. The most modern of these techniques (intensity modulated radiation therapy (IMRT), image guided radiation therapy (IGRT), high dose rate remote afterloader brachytherapy) try to conform the high dose of radiation to the region of malignant disease while avoiding delivering dose to as much normal tissue as possible.

However, modern day radiation therapy may have reached its limit in terms of its ability to eliminate or control cancer, especially for invasive cancers where the malignant cells intermix with normal cells such that killing the former also will kill the latter. Even with IMRT it is impossible to create a conformal enough dose distribution such that all cancer cells are destroyed but all normal cells are spared. IGRT reduces the amount of normal tissue that is included in the treatment volume but cannot eliminate it entirely. Although metabolic imaging techniques can provide additional information about cancer location, the designation of a target volume is still a physician-based process, fraught with inter- and intra-user variability and with an inability to differentiate disease from normal at the cellular level. In addition, many cancers contain radioresistant regions in their center due to poor oxygenation. It is not until the surrounding well oxygenated cells are destroyed that oxygen can be delivered to the interior, thereby making these cells more radiosensitive. However, the amount of radiation required to kill the initial group of oxygenated cells uses up all of the normal tissue reserve; the interior cells once oxygenated cannot be treated with additional radiation without destroying surround normal tissue.

Thus it is possible that without a paradigm shift in the way radiation therapy is delivered the physician-defined target-directed radiation therapy of today probably is nearing its maximum capability as a cancer-fighting therapy.

Binary Therapy

The limited efficacy and extended toxicity of traditional single agent cytotoxic therapy such as radiation therapy has led researchers to explore the design and development of targeted binary therapies that differentiate between, and thereby augment the effect on, malignant cells as compared to nonmalignant cells. A binary therapy is an approach that utilizes two agents, each of which by itself has no cytotoxicity but when used in concert become tumorcidal. In theory, if one or both of the two agents can be restricted to the cancerous cells only, then the therapy can have an extremely high therapeutic ratio (ratio of dose delivered to tumor versus dose delivered to tissue) with much less toxicity than conventional therapies.

A number of binary therapies are under development; those based on or including the use of radiation often are called radiogenic therapy. Although external beam MV radiation is being explored as a means of activating chemotherapeutic agents (an inactive "prodrug" is converted to an active drug by the MV radiation) or gene vectors (an antitumor "pro-gene" injected into the tumor is converted to an active gene by MV radiation), it is believed that one of the more promising approaches is based on the principle of dose enhancement through Auger electron emission.

When an x-ray encounters an atom, it interacts through one of three processes: photoelectric absorption, elastic scattering, or Compton scattering. The relative probability of each interaction is a function of the x-ray photon energy. In Compton scattering, an incident photon loses enough of its energy to an outer orbital electron to cause its ejection. This electron has an energy equal to that lost by the photon as a result of the interaction, and can be quite sizeable. The original photon continues on its way but in a new direction, with a lower energy, and with the potential to interact again at any distance. Compton scattering is thought to be the principal absorption mechanism for x-rays in the normal therapeutic range of 100 KeV to 10 MeV (million electron volts) and is relatively independent of the atomic number of the absorbing material.

The photoelectric effect is the most efficient means for conversion of x-ray energy to ionization in the body and is believed to dominate at low energy (10-120 KeV). It is a process whereby a photon, of an energy near the absorption energy of an inner electron shell in the target material, transfers its entire energy to the electron that subsequently is ejected from the atom (photoelectron). The relatively low kinetic energy of the ejected photoelectron is equal to the incident X-ray photon energy minus the binding energy of the electron. The vacancy in the electron orbital resulting from the electron ejection is filled by an electron from an outer orbit (with a lower binding energy), leaving a vacancy in this outer orbit that in turn is filled by another electron from an orbit even further away from the nucleus. The surplus energy liberated when an electron drops from an outer shell to a shell closer to the nucleus results either in the emission of a fluorescent photon or in the ejection of an additional secondary electron (Auger electron) from the same shell. If Auger electron emission occurs, the atom is left in a doubly ionized state (due to two ejected electrons) that is resolved by the dropping of other electrons from outer shells to fill the holes. This cascade process results in the release of a large number of very low energy electrons that travel very short distances and deposit their energy (track ends) locally (therefore with a very high linear energy transfer (LET)). If the electrons are produced near the DNA they can be very effective in killing the cell through double strand breaks.

The depth of penetration of Auger electrons is very small, on the order of 1-10 micrometers. Thus reliable cell death requires that the Auger electron be generated within 1-10 micrometers of the DNA, e.g. within the cell (and preferably within the nucleus) itself. The disadvantage of this approach is that the process for generating the Auger electrons must take place within the cell. The advantage is that the tumorcidal effect of the radiation is limited to the target cells. As a result, such a therapy has the potential for repetitive dosing with minimal toxicity.

Dose Enhancement

Auger electrons at a target site can be increased significantly if a high Z material is introduced into the target as long as the energy of the radiation is at or near the K, L, or M electron shell binding energies for the high Z material. The radiation interacts with the high Z material that, because of the energy match between the radiation beam and the material's greater density of electrons (as compared to tissue), produces auger electrons in great numbers. This process is known as dose enhancement; the local deposition of dose is increased due to the presence of a high z material. Dose enhancement with high Z materials is minimal or absent at high radiation energies because of the limited number of photoelectric interactions that occur at megavoltage energies due to the fact that the binding energy of high Z materials are in the low energy range.

Depending on the element, concentration of element, and low energy photons used, the local dose may be increased by as much as 150 fold or more. Contrast material has been used traditionally as the dose enhancement agent in conjunction with orthovoltage x-rays in order to produce an increase in the level of dose by a factor of 0.5 to as much as 2 or more depending on energy and concentration of agent in the tissue (the higher the concentration, the greater the dose enhancement). Contrast agents contain typically a large percentage of a heavy element from the upper half of the periodic table such as iodine or gadolinium; it is the interaction of the othovoltage x-rays with the element that results in the dose enhancement. Because tumors usually contain "leaky" blood vessels, contrast material injected in the vascular system will find its way into a tumor through extravasation from these blood vessels. In fact historically, it is the region of contrast enhancement that is designated as the target volume for radiation therapy treatments.

It is important to note that contrast agents identify regions of disruption of vascular and by extension indirectly identify regions that may contain cancer cells. However, these agents do not identify cancer cells directly. Thus by using a contrast agent alone to generate dose enhancement, it is possible not only to kill normal cells contained within the region of contrast enhancement but to not identify cancer cells that lie in regions that do not enhance, or where the concentration of cancer cells is too small to cause vascular disruption. In addition, it is often difficult to deliver enough contrast agent to the region in question by the IV route in order to achieve significant enough dose enhancement. Direct injection allows for a higher concentration of contrast agent, but it requires an invasive procedure that may not gain access to all tumors.

There are other materials that have been explored for dose enhancement with radiation of all types, namely gold particles of any size, and other ways of delivering the particles to the tumor so that only abnormal cells are labeled or are labeled preferentially, namely using antibodies, oligonucleotides, nucleotide analogues, amino acids, and dendrimers. Gold nanoparticles are inert and biocompatible and the gold surface provides a simple chemistry for the self-assembly to labeling materials thereby encouraging the nanoparticles to accumulate in the vicinity of, or directly inside, malignant cells. They can be delivered by IV injection or sprayed/injected directly onto/into the target (if accessible) and can accumulate in concentrations sufficient to blanket all cells in the target volume. Gold nanoparticles, when used in the presence of 50 kvp radiation, are predicted to result in a dose enhancement of as much as 150 fold based upon published studies performed with thin gold foil. However, the actual enhancement able to be obtained in a clinical setting is dependent on the percent of the total mass contributed by the gold. With reasonable levels of 0.3-3% that are obtainable clinically, an enhancement level believed to be on the order of 2-10 fold can be expected.

The differential dose enhancement of tumor cells versus normal tissue only occurs if the high Z material is linked to tumor cells and not to normal cells. Means for achieving such in the past have centered on the use of contrast agents; the agent leaks out of highly permeable vasculature in the tumor to stain the tumor and not surrounding normal tissue possessing normal vessels. However, ideally one would like to target the tumor cells directly, thereby allowing direct differentiation between normal and abnormal cells. Since the enhanced effect from Auger electrons are believed to occur predominantly in the cells where they are generated, direct targeting of abnormal cells could allow the destruction of an abnormal cell while sparing an immediately adjacent normal cell.

Problems with Low Energy Radiation

The major downside to low energy x-rays that limits their use in dose enhancement applications is their very poor penetration in tissue as described previously. At a depth of 20-30 cm, the residual dose from a 50-70 KV beam, the optimal energy range for gold dose enhancement, is about 0.001-0.1% of its maximum dose; even at a maximal 10× enhancement no more than 1% of the maximum dose at the surface will be delivered at depth. This can be improved by using multiple fields to deliver the treatment, such as is used in radiosurgery, thereby spreading the dose to nontarget tissue out over a larger area. However, even using 10 fields will only result in a dose at depth that is at best equal to 10% of the dose at the skin.

A range of approaches such as optically focused beams and rotational x-ray sources have been used to increase the dose of low energy radiation deposited in deep targets that would interact with dose enhancement agents; these were described previously. Unfortunately, the same problems discussed previously that apply to each of the low energy x-ray delivery approaches without the use of dose enhancement apply to their use with dose enhancement, namely a high cost, complexity, a lack of portability, lengthy treatment times, and limited available geometries restricting applicability, apply when used with dose enhancement. Another approach that has been explored is with the use of a monenergetic beam of radiation produced by a synchrotron that is able to deliver the required radiation at a much faster rate. Unfortunately, this is a $100 million device based on a cyclotron that limits severely its availability and suitability.

Thus there still is a need to develop a realistic, practical, cost and time efficient, portable, universally available, easy to manufacture, and easy to use means of delivering in a single or few fractions to cancer cells deep in a patient a dose of radiation sufficient enough to be able to benefit from the dose enhancement possible with high z materials delivered selectively to the target without producing too much dose of radiation in other portions of the patient and especially at the tissue surface.

SUMMARY

This present invention provides methods and apparatuses for performing radiation therapy with low energy x-rays on a selected region of tissue in a patient in proximity to the apparatus whereby the amount of radiation delivered to the region can be equal to or greater than the dose delivered to the tissue or other material through which the radiation passes. It also provides methods and apparatuses for fully automating the process, from treatment region identification through treatment planning to treatment delivery, and can be used to treat regions on or below the surface of tissue, in a cavity and underlying region created following a surgical resection, on or below the surface of an internal cavity, hollow viscus, or lumen, or deep in tissue adjacent to an inserted probe or conduit or catheter.

The preferred embodiment employs a small tabletop stationary five-degree of freedom device such as a "robot" that is used to define the treatment region by tracing the region under direct visualization and then to precisely deliver the treatment plan created by an automatic planning system by positioning a single low energy radiation source, or a plurality of low energy sources connected to each other in a predetermined parallel or similar geometry, each of which may be equipped with blocking and attenuation mechanisms, at a plurality of positions in a planar fashion across or through a selected treatment field, thereby delivering a plurality of parallel overlapping beams indexed on a millimeter or submillimeter grid such that a concentration of dose is achieved at a variable depth in tissue relative to the dose where the radiation first enters the tissue.

The present invention also provides methods and apparatuses for creating with low energy x-rays a high dose of ionizing radiation in unhealthy tissue, such as tumors, at any depth while maintaining low dose in all other healthy tissue regardless of its location. The method employs the use of low energy radiation delivered at a high enough dose at any depth such that sufficient secondary radiation can be generated through the use of dose enhancement agents such as nanoparticle gold such that a complete tumorcidal dose of radiation can be delivered in as little as a single treatment session without damage to any nontumor tissue. The preferred embodiment employs a scanning beam electron device, including means for attenuating and blocking the beams of radiation, used to generate a plurality of overlapping beams indexed on a millimeter or submillimeter grid that converge on a target volume loaded with gold nanoparticles, thereby delivering a tumorcidal dose of radiation to tumor cells but not to normal cells within or outside the treatment volume.

OBJECTS AND ADVANTAGES

The benefits of this invention are many. These include:
(a) the ability to create a range of depth dose curves using a low energy source such that a range of lesions of different thickness in close proximity to the radiation source can be treated;
(b) the ability to create depth dose curves using a low energy source where the dose at depth in tissue can be greater than the dose at entrance into tissue if desired or where the dose at depth can be the same as the dose at entrance into tissue;
(c) the automatic nature of the planning process for delivering such a dose, thereby eliminating the need for preplanning the treatment;
(d) the real-time patient-based nature of the target definition, thereby eliminating or reducing the need for, and error associated with, preimaging and delineation of the target in software;
(e) the automatic delivery nature of the dose, thereby eliminating the need for the user to be at the patient side when the treatment is delivered, thus reducing issues associated with shielding the user from radiation;
(f) the precise nature of the treatment delivery, thereby potentially improving outcome.

Further benefits and advantages of this invention include:
(a) the ability to deliver a tumorcidal dose of radiation to a target volume not in close proximity to the radiation source without delivering significant dose to nontarget tissue regardless of its location;
(b) the ability to vary the depth at which dose is delivered by varying either the energy used to deliver the treatment or the focal point of the treatment, whichever is more appropriate given the clinical conditions;
(c) the ability to differentiate normal from abnormal tissue within a targeted treatment volume and to use that differentiation to effect different levels of radiation.

This invention will allow targets in close proximity to the radiation source, such as the skin, operative cavity, lumen of a hollow viscus vessel, or deep target accessed by a catheter, to be treated in highly precise and tailored manner regardless of their location. Furthermore the combination of a low energy delivery device delivering increased dose at depth and nanoparticle dose enhancement will allow all tumors regardless of depth or location to be treated to a very high dose in a single or few sessions without incurring damage in surrounding normal tissue or overlying skin. It will eliminate the need to worry about minor patient movement during treatment and reduce the complexity of equipment used to deliver radiation therapy treatments. It also will allow such a treatment to be delivered with relatively low cost equipment in an outpatient setting with minimal if any radiation shielding. Furthermore, it will allow noncancerous cells within a tumor to be spared and will allow cancerous cells outside of a localized tumor to be destroyed without damaging the tissue within which they reside.

In summary, the apparatus and methods disclosed will allow low energy radiation to be used in a much greater range of clinical applications than would otherwise possible.

BRIEF DESCRIPTION OF THE DRAWINGS

FIGS. 1A, 1B, 1C, and 1D show normal depth dose curves from a KV x-ray source disposed in typical treatment scenarios.

FIGS. 7A, 7B, 7C, 7D, 7E, and 7F shows means for producing variable beam blocking or shaping or collimation.

FIG. 13 shows examples of depth dose curves resulting from the use of this invention.

FIG. 14 shows a means for producing indexed beams of radiation.

FIG. 15 shows a means for grouping radiation sources together to produce indexed beams of radiation.

FIG. 19A to 19B shows a means for defining and capturing electronically the region to be treated.

FIGS. 20A, 20B, 20C and 20D shows a graphical tool for inputting required delivery information.

FIG. 21A to 21B shows a means for determining if the treatment region has moved once data has been acquired.

FIG. 22 shows an alternative means for determining if the treatment region has moved once data has been acquired.

FIGS. 25A, 25B, 25C, 25D, 25E, 25F and 25G shows collimator plates formed to generate different shaped and directed beams of radiation.

FIGS. 27A, 27B, 27C and 27D shows a variable collimator design modified to deliver convergent beams.

FIG. 28A is for unmodified kvp beams; FIG. 28B is for modified kvp beams to a 4 cm target; FIG. 28C is for modified kvp beams to a 10 cm target.

DETAILED DESCRIPTION OF THE INVENTION

Targets in Proximity to Treatment Device

Figure 2A:
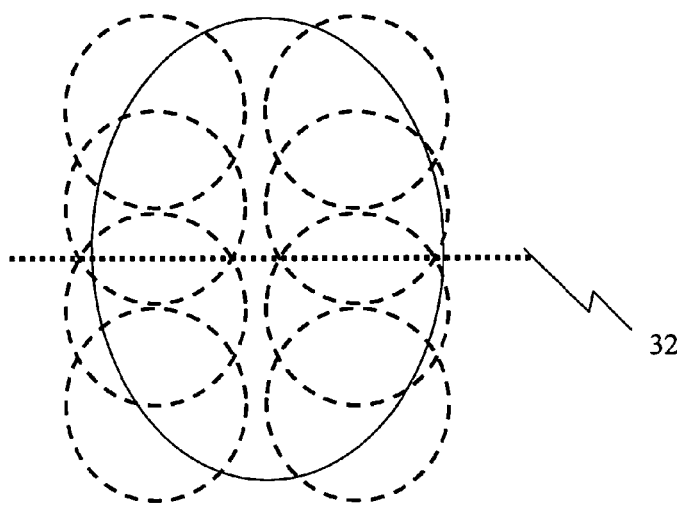
FIGS. 2A, 2B, 2C, and 2D show normal depth dose curves from a KV x-ray source disposed with multiple beams to cover a large target.
Figure 2B:
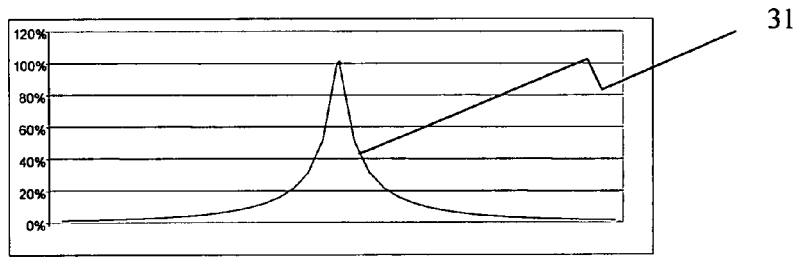
Figure 2C:
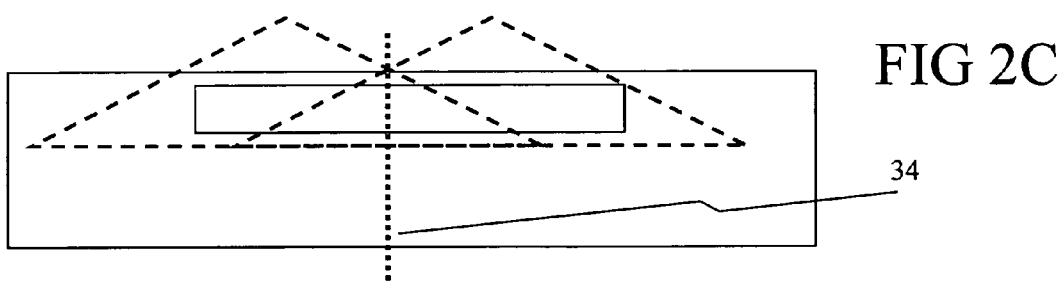
Figure 2D:
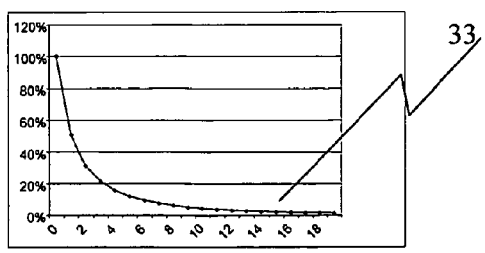

In the preferred embodiment a low energy x-ray tube with an energy ranging from 20 KV to 120 KV that is as small as 1 mm or less in diameter can be used as the source of radiation. Such tubes have been described by many and are now in commercial production. Radioactive sources of radiation or larger x-ray tubes also can also used with an appropriate increase in the size of all other components to be described, although as the size of the radiation source construct increases, the fewer are the areas that can be reached by the construct due to collision between the construct and the surrounding anatomy. The % dose versus depth in tissue curve from low energy x-rays 321 in FIG. 1B along the plane 326 in FIG. 1A delivered from such a low energy radiation source 322 that spreads 323 and is impingent on a target 324 in a patient 325 does not fall off in a pure exponential manner as is the case with megavoltage (MV) x-rays. Much of the beam that is emitted by such a small kvp x-ray device consists of very low dose photons that are attenuated very rapidly in very small thicknesses of tissue. Therefore an increased amount of dose is deposited at or very near the skin surface when compared to filtered KV devices or MV devices. It is this increased deposition at skin surface that in part makes low energy radiation difficult to use in many treatment applications. It is also the fact that because of the low energy even filtered KV beams do not penetrate very deep in tissue. This is the case whether the beam of radiation is emitted from the end of the source 323 in FIG. 1A or circumferentially 327 in FIG. 1C around the source producing curve 329 in FIG. 1D along plane 328 in patient 325 in FIG. 1C. Targets that require the overlap of more than one beam simply to achieve coverage of targets that are greater than the size of a single beam are still plagued by this same problem, as shown by curve 31 in FIG. 2B along plane 32 in FIG. 2A and curve 33 in FIG. 2D along plane 34 in FIG. 2C.

Attenuation

Figure 3A:
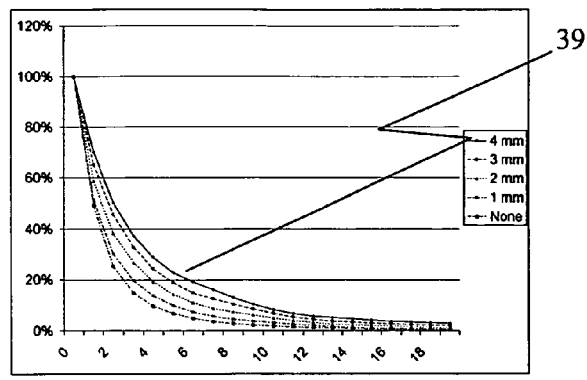
FIG. 3A to 3B show the depth dose curves from a KV source with variable attenuation.
Figure 3B:
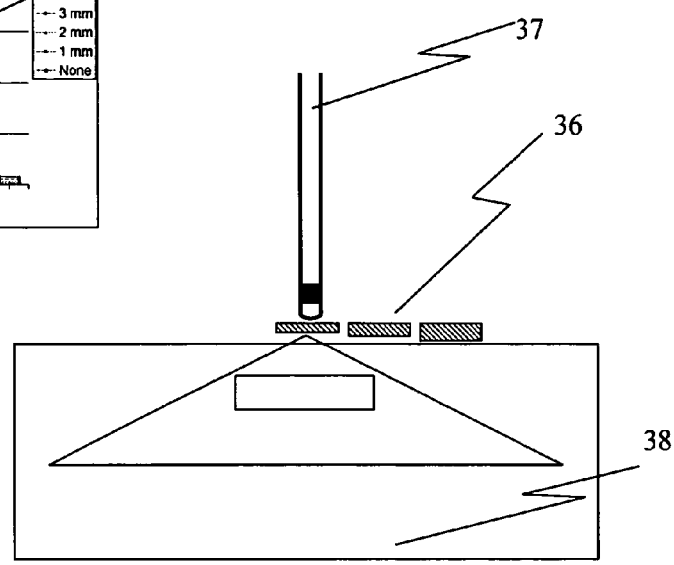

The magnitude of this problem can be reduced by interposing a variable thickness of attenuating (also known as filtering or hardening) material 36 between the x-ray source 37 and the patient 38 in FIG. 3B such that beam hardening can occur. By filtering out much of the very low energy x-rays prior to the beam interacting with tissue, the shape of the curves 39 in FIG. 3A showing % dose versus depth for different thickness of attenuation once the beam enters the tissue become less steep and therefore the dose at the surface relative to the dose at depth is reduced. In essence, as the amount of attenuation material is increased the beam becomes more and more like a monoenergetic beam that has a true exponential depth dose curve.

Figures 4A, 4B:
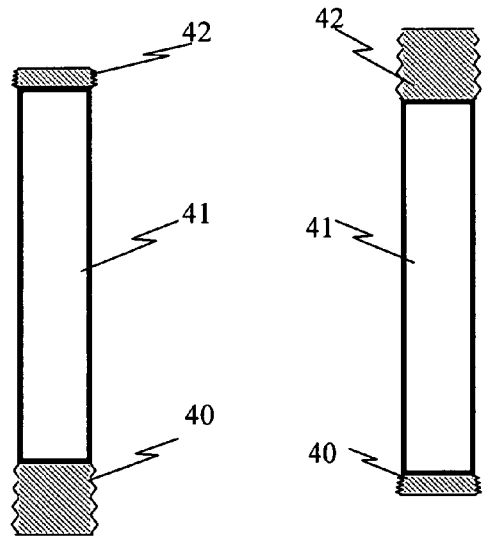
FIGS. 4A, 4B, and 4C shows a means for producing variable attenuation or hardening and resulting sample depth dose curves.
Figure 4C:
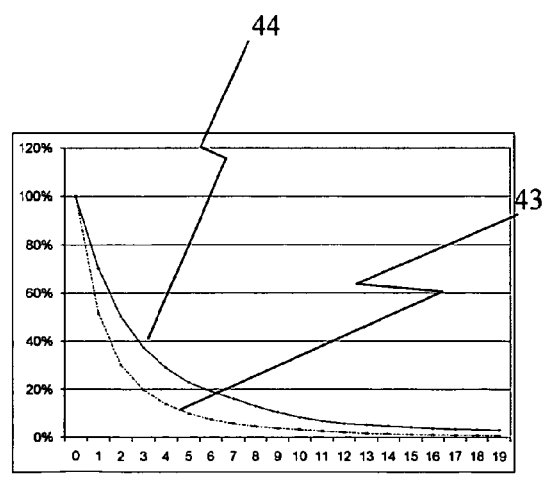

The thickness of the attenuating material secured to the radiation source can be varied by several means. The preferred means involves the use of a device whereby the amount of attenuation can be varied, such as the small bellows 40 in FIG. 4A and FIG. 4B filled with water or some other attenuation material that is fitted to the end of the radiation tube 41: the higher the attenuation or the density of the material the better; for instance mercury or some other flowable high density material such as a tungsten slurry is ideal. By varying the length of the bellows while keeping it filled with the chosen material by drawing it from a reservoir 42, the amount of attenuation between the beam and the patient can be varied very finely, producing the curves for one mm of water attenuation 43 for instance and 44 for four mm attenuation. The effective attenuation that is preferred is the equivalent of anywhere from 1-5 mm of tissue. By using a high attenuation material the thickness required to achieve this amount of effective attenuation can be reduced to less than 0.1 mm equivalent per mm of tissue.

In this embodiment, the bellows is made of a material that will not degrade in the presence of low energy radiation, such as mylar or a thin low density metal. The bellows is filled from a pressurized reservoir. Bellows length can be changed by increasing/decreasing pressure in the reservoir after the pressure/length ratio has been measured experimentally. Alternatively, the length can be changed by physically pushing/pulling the end of the bellows through the use of small arms attached to the end of the bellows, the length controlled by monitoring the change in length of the arms through potentiometers attached to the motors driving the arms or through other suitable means. In addition, if the lengths are changed asymmetrically, a wedge type distribution can be created.

Figure 5A:
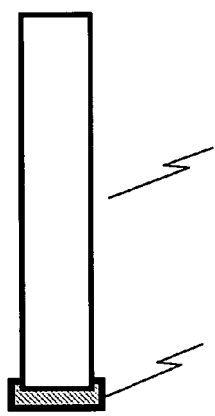
FIGS. 5A and 5B shows an alternative means for producing variable attenuation.
Figure 5B:
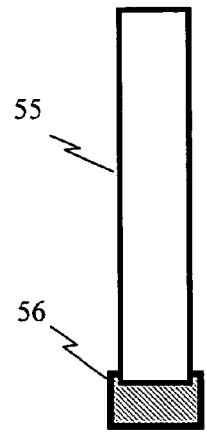
Figure 6:
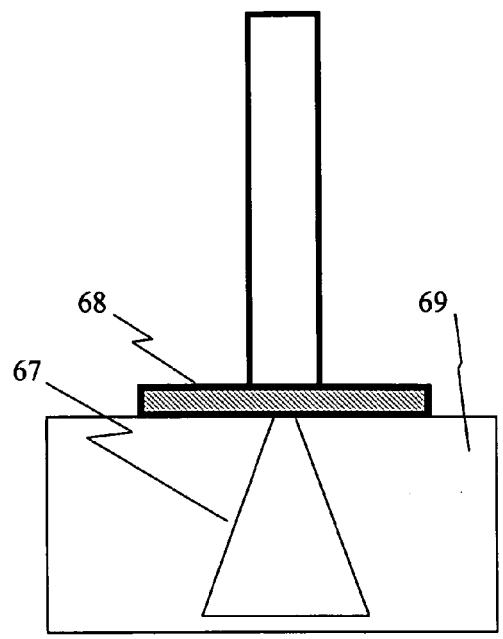
FIG. 6 shows an alternative means for producing fixed attenuation.

In another embodiment, the attenuation can be provided by a range of small caps 56 made of attenuation material that fit over the end of the x-ray tube 55 as in FIG. 5. These caps can be secured manually by the user or can be selected automatically by the small robot described in FIG. 14 using a "pluck and play" mechanism similar to that used by computer-controlled milling machines. Each cap would have a different thickness of the same material or the same thickness of different materials such that, by choosing the appropriate cap, the desired attenuation can be achieved. Any other means for varying the thickness of material at the end of the tube can be used as well. In addition, attenuation can be achieved by laying a piece of attenuating material 68 in FIG. 6 over the region in question 69 so that the radiation beam 67 passes through the material prior to entering the tissue overlying the region to be treated.

Collimation

Figure 8:
FIG. 8 shows an alternative means for producing variable beam blocking or shaping or collimation.
Figure 9:
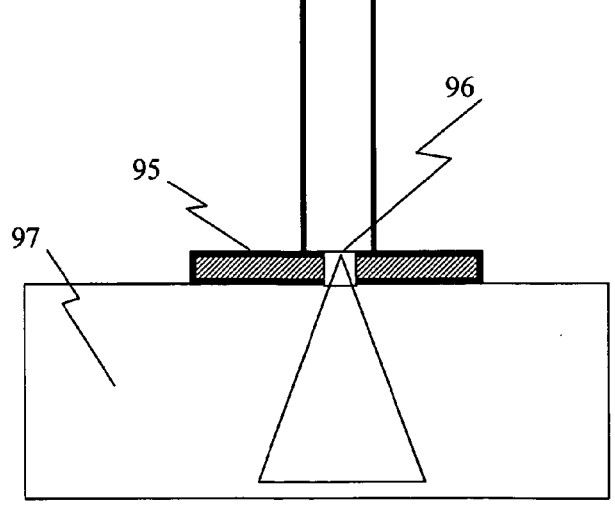
FIG. 9 shows an alternative means for producing beam blocking or shaping or collimation.

The amount of spread of the radiation beam also must be controlled as this determines how much tissue a beam will hit as it passes through the patient or conversely how much tissue a beam is able to cover. A variety of different beam shaping devices have been created in the past and can be used in miniature form with the small x-ray tube that is part of the preferred embodiment of this invention. For such a small beam, FIG. 7 depicts beam shaping accomplished in one of two general manners; the beam shaping material 71 can be lengthened/shortened relative to the end of the radiation source by moving it closer to or farther from the end of the radiation source or the opening formed by the beam shaping material 73 can be increased or decreased. Either approach can be used with this invention and will change the amount of beam spread 72. The former can be implemented as in FIG. 8 by using a cylindrical housing or bellows 84 that is extendable and that is filled with a radioopaque blocking material much in the manner used with the attenuator. By extending the bellows, the length of the shaping material is increased and limits the spread of the beam. It also can be implemented by fixed length metal blocks that are raised and lowered by a mechanical linkage driven by a motor. The latter approach can be implemented by pairs of blocks of fixed height that are driven in/out through a linage attached to a miniature motor, thereby changing the size of the opening between the blocks and thus the beam spread. In addition, any other means commonly in practice can be used to shape the beam. Although it is desired that the ability to change the spread of the beam be adjustable during the course of treatment, blocking or beam shaping can be accomplished in a non-variable manner as well. For instance, a sheet of material 95 that is opaque to the radiation beam and contains at least one aperture 96 of known but variable size acting as radiation transmissive can be laid over the surface of the region to be treated 97. By having a range of sheets each with apertures of a specific size, different amounts of blocking can be implemented.

The use of a beam shaping device will control the spread of the beam and the use of an attenuation device will change the speed of dose fall-off. However, the resultant depth dose curves will all be of the same general shape for a single beam—greatest dose at the surface with dose decreasing with depth—and will be fixed as a single curve for a given energy and amount of attenuation. These modifications or steps do not allow one to change the shape of the depth dose curve and the percentage of dose at depth to fit the clinical needs. An additional aspect of the present invention will allow the actual shape of the curve to be changed so that maximum dose can be deposited at a depth other than the surface, or over a larger distance, as determined by the requirement of the treatment.

Disposing Beams in an Array

Figure 10A:
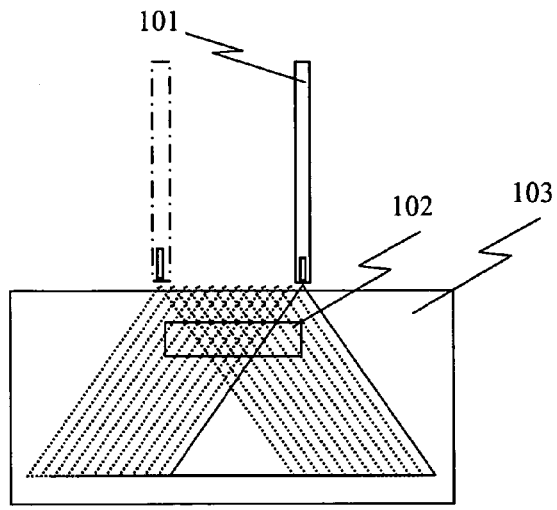
FIGS. 10A, 10B, 10C, and 10D shows the delivery geometry for the preferred embodiment.

As mentioned previously, treating a volume of tissue in proximity to the radiation source located on or below the surface of the patient, in a cavity and underlying region created following a surgical resection, on or below the surface of an internal cavity, hollow viscus, or lumen, or deep in tissue surrounding an inserted probe or conduit or catheter, calls typically for covering the entire target with a single beam of radiation if the volume is small or using several beams of radiation that minimally overlap in order to cover the volume if it is large. In the present invention, a very large number of beams are used to cover the target regardless of its size with no requirement that the entire target be covered by any given beam of radiation. Instead, increased dose at depth is achieved by precisely indexing the beam 101 in millimeter or submillimeter increments across the target 102 in patient 103 as in FIG. 10A, with each portion of the target being covered by a very large number of beams.

Figure 10B:
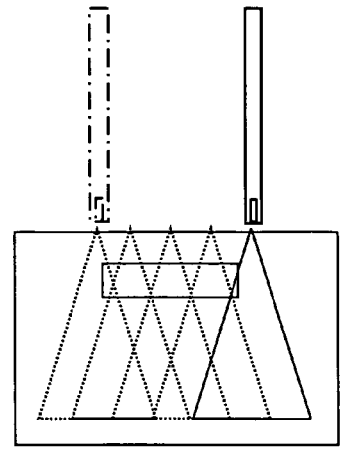
Figure 10C:
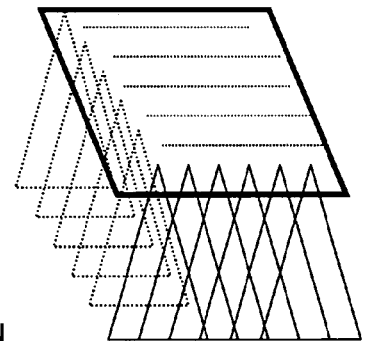
Figure 10D:
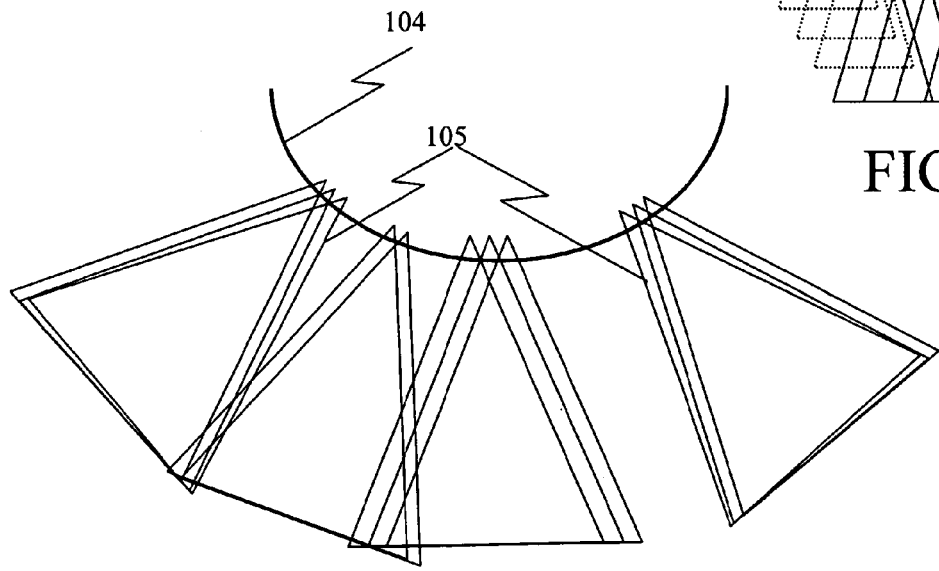

Each beam will increase the region that it encompasses as it passes farther from the source and deeper into tissue due to the spread of the beam. As the beam spreads it will overlap with other beams to a greater and greater degree. As the beams overlap the radiation contained in the beams will add together, increasing the dose delivered to any given spot within the target volume relative to that received by a single beam. At the same time, the area of tissue at the point of beam entrance will receive radiation from one or at most a few beams. This tendency for the total dose to increase with depth due to overlapping of beams is counteracted by the tendency of the dose from any given single beam to decrease with depth as the beam is attenuated by the tissue through which it is passing. Depending on the size and shape of the beam and the size of the index distance, the amount of overlap will vary, with some geometries resulting in an increase or a decrease in the number of beams that cover any given portion or all of the target (FIG. 10B). By varying the spread of the beam, the attenuation of the beam, and the spacing between or index of the beams, these two opposite tendencies can be controlled in order to create different amounts of relative total dose deposited at any given depth and therefore the shape of the depth dose curve. As long as the number of beam overlaps increases with depth and not at the tissue surface, the effect will be to reduce the amount of dose at the tissue intercept surface relative to the amount of dose at depth. In the preferred embodiment of the present invention each of the many beams of radiation is delivered from a planar indexed position relative to the first beam forming a one or more dimensional array of beams where all beams are parallel to each other (FIG. 10C). However, other pseudoparallel geometries are possible, such as one required to treat surgical cavities 104 in FIG. 10D where each beam 105 is directed orthogonal to the tissue surface through which it must pass, some of such beams shown.

The actual index amount used to deliver a treatment will depend on a number of factors including the size of the electron target that is the part of the x-ray source used to generate photons, the shape, size, and amount of blocking used to configure the beam, the desired depth dose curve, and the distance the radiation device is from the tissue surface through which beams of radiation will be passing. In general, the index amount will be one that causes the beams of radiation emitted by the source to begin to overlap just at the tissue surface. Thus the index amount will be greater for beams with a steep angle of spread then for beams with a shallow angle of spread, will be greater for a delivery device that is removed from the tissue surface than for one that is in direct in contact with the tissue surface, and for a delivery device with a photon generating target of a millimeter or more than for one with a submillimeter target (the larger the target, the wider is the penumbra and therefore the greater is the effective beam spread). Regardless, the index amount given the normal range of radiation devices for which this invention is expected to be used is in the submillimeter to several millimeter range.

By adjusting simultaneously the amount of attenuation, the spread of the beam, and the spacing of beams, it is possible to create a wide range of depth dose curves. In addition, by varying the beam energy, it is possible to increase even further the range of depth dose curves that can be created (FIG. 13). This ability to vary the shape of the depth dose curve is of value for superficial and deep conditions alike, the sole criteria being a need to alter the delivery of radiation to the target volume from one where the dose when the radiation first enters tissue is very much higher than the dose at any distance from the radiation source to one where the dose at some distance from the radiation source is equal to or greater than the dose when the radiation first enters the tissue.

Medical Applications

There is a medical value in being able to vary the depth dose curve in this manner. There are various superficial diseases that can benefit from radiation treatment that lie at different depths below the surface of the skin yet within the range of treatment possible with KV or orthovoltage radiation. For instance, some skin cancers require treatment only to a depth of several millimeters while more advanced disease may require treatment at a deeper depth of a centimeter or more. With unmodified KV radiation, only a single depth dose curve is possible with maximum dose delivered to the skin: to deliver adequate dose at depth will require delivering too much dose to the skin surface. With this invention, as can be seen in FIG. 13, a treatment dose can be delivered from skin surface to as much as 1 cm deep by 133.

Alternatively, the maximum dose 131 can be moved below the surface to a depth of as much as five mm or more with skin sparing. As another example, keloids are a condition that requires sufficient dose delivered to the skin surface and at least two millimeters below the skin surface. With this invention, as seen with 132, dose is within an acceptable range from the skin surface to this two mm depth and then falls off rapidly. For IORT applications, it is desired that dose be delivered to some arbitrary depth is tissue below the surface of the exposed surgical cavity. However, prior to this invention, if the dose at the immediate surface is too high, the dose required at depth to destroy remaining cancer cells cannot be achieved without destroying tissue at the surface. With the herein described approaches, it is possible to deliver dose at depth while not delivering an excessive amount of dose to the tissue surface.

In addition there are other applications where the treatment of small volumes of tissue cannot be achieved because the dose in the portion of the volume near the x-ray source is too great relative to the dose some distance from the x-ray source. For instance, in FIG. 11A assume 2 mm radiation probe 109 is inserted in tissue volume 110. 112 describes the typical spread of the dose that would result from a single position of the 2 mm x-ray source emitted from an active target region 111; the dose spread would be similar for a radioactive source. The depth dose curve along 113 would look like 114 in FIG. 11B. It is possible to overlap many beams with indexing as described herein and depicted in FIG. 11C. However, because the beams overlap at their origin as in region 113, there is no increase in dose at depth compared to the surface and the depth dose curve along 116 would look the same as 114 in FIG. 11B.

Figure 11A:
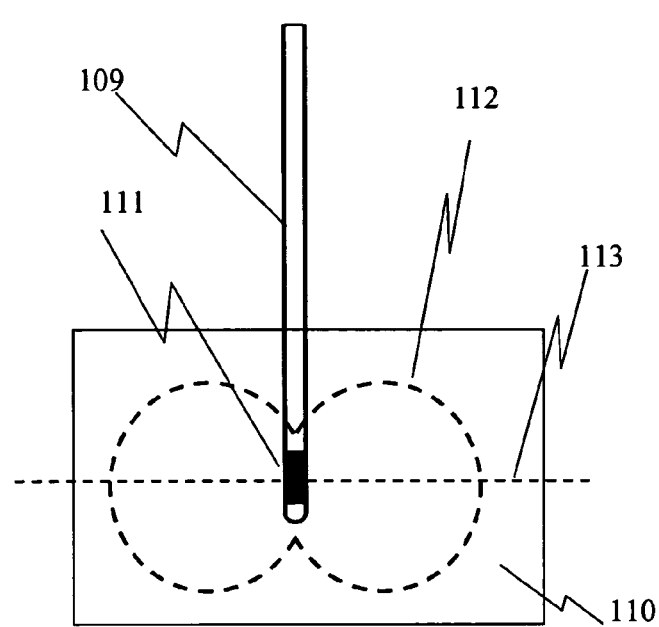
FIGS. 11A, 11B and 11C shows a treatment probe inserted into a body cavity and the resulting delivery and depth dose curves.
Figure 11C:
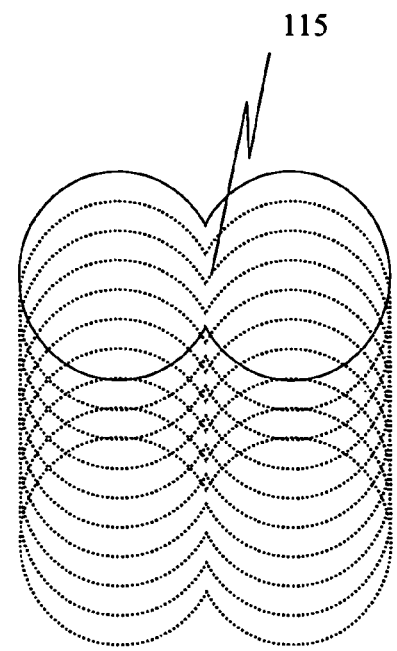
Figure 11B:
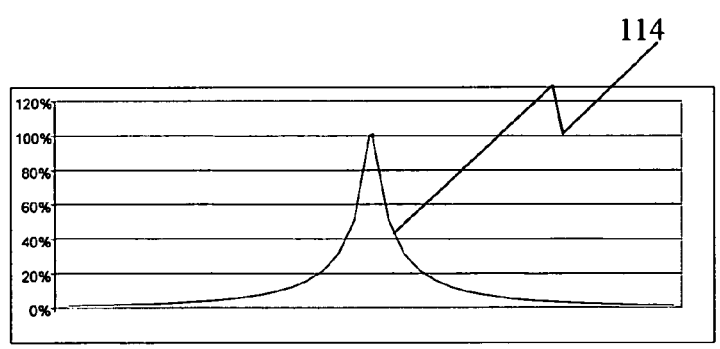
Figure 12A:
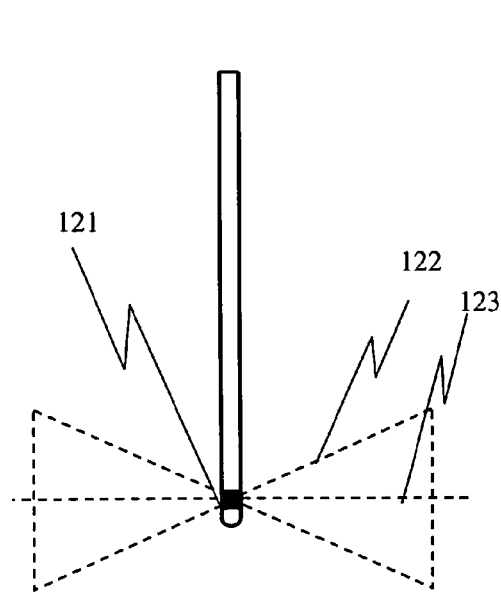
FIGS. 12A, 12B and 12C shows a treatment probe inserted into a body cavity with a modified delivery geometry.
Figure 12B:
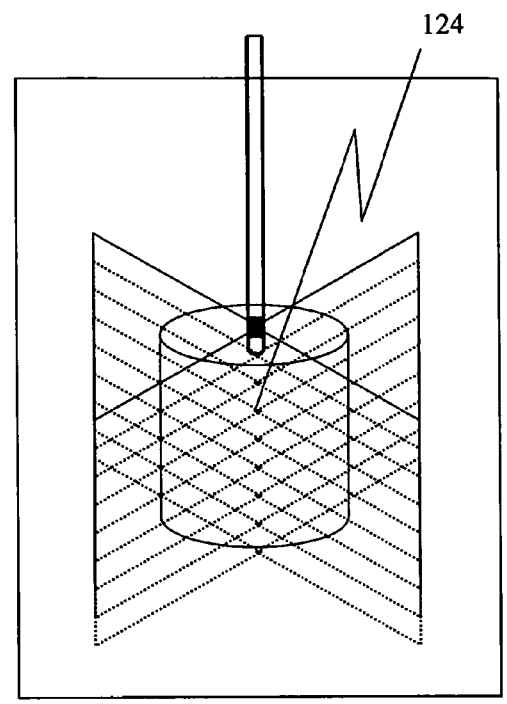
Figure 12C:
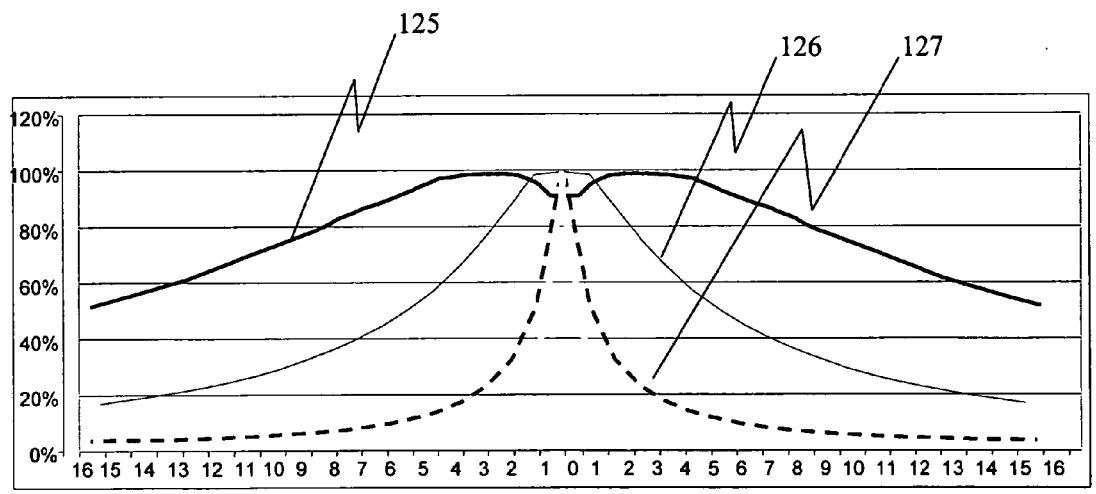

If the electron target in the x-ray probe was reduced in size 121 in FIG. 12A and/or as in the preferred embodiment the beam was blocked so as to produce dose spread 122, the depth dose curve for a single position of the probe would still look like 113 in FIG. 11A. However, if now the beams are indexed as described herein there is overlap of beams at depth but not at the surface 124 in FIG. 12B and curves such as 125 and 126 in FIG. 12C are possible. This compares favorably to the curve 127 that would result from normal delivery as is practiced routinely today.

Robot for Implementing Array

Since the degree of beam overlap is the primary determinant of the variation in depth dose it is required that the beams be positioned precisely so as to achieve the desired degree of beam overlap. The preferred means of implementing the indexing of the radiation source is achieved as in FIG. 14 by securing the small x-ray tube 141 to the arm or attachment point of a small multiple degree-of-freedom manipulator or device 142 such as a table-top robot or a multiple-stage translational/rotational manipulator or device. This device allows the x-ray tube to be moved around with unlimited freedom but under computer control. It is required that the robot be able to translate the x-ray tube over the surface of the region to be treated and to raise and lower the tube. It is desirable but not required that the device be able also to angulate the tube relative to the region to be treated as this increases the range of conditions that can be treated and the range of delivery geometries that can used. It is also desirable but not required that the x-ray tube be able to rotate around its central axis relative to the region to be treated. In the preferred embodiment the small multiple degree-of-freedom manipulator or device 142 sits on a cart 143 that includes also a display terminal 144 for interacting with the system as well as a place for attenuators (if caps are used), a computer, a keyboard, and a power source. The cart has a locking system to prevent the cart from being moved once treatment begins. The cart may also include the treatment planning computer and software as well as the localization system to be described below if this is separate or different from the robot. At the time of treatment the robot will position the x-ray tube over the region to be treated and, after the beam is activated for the prescribed amount of time, will precisely index the position to the tube in order to deliver the next beam, repeated as required. If multiple x-rays tubes are used connected together in a known geometry 153, then the robot will carry this assembly and will index the assembly after the first beam-on time 152 so that the resulting array of beam positions will meet the plan requirement (FIG. 15).

Scanning Electron Beam for Implementing Array

Figure 16A:
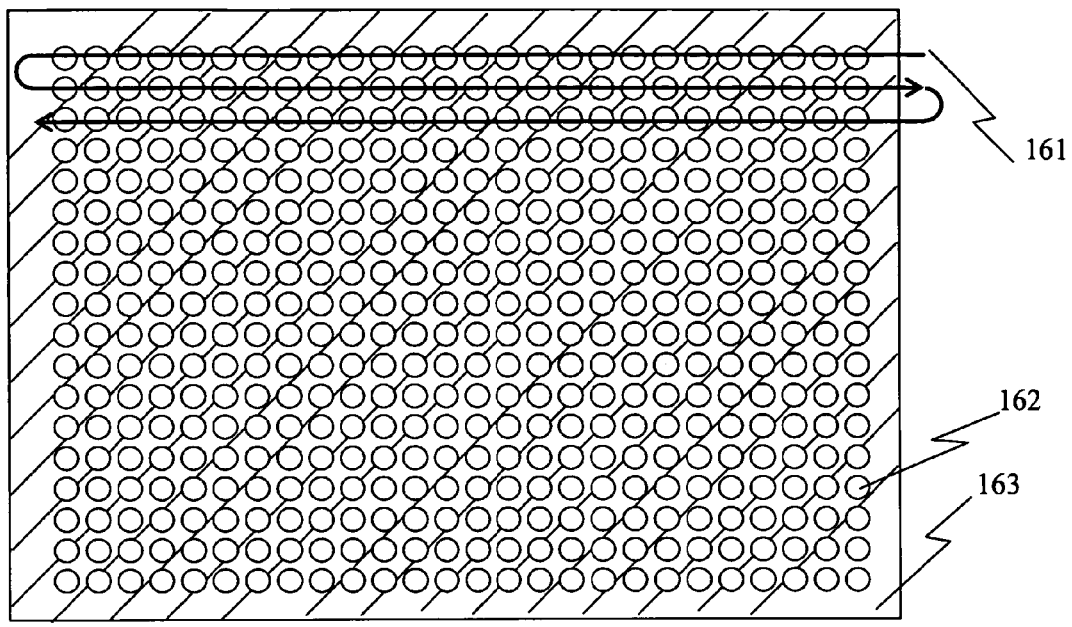
FIG. 16A to 16B shows two views of an alternative means for producing the desired result using a scanning electron beam instead of a fixed x-ray source.
Figure 16B:
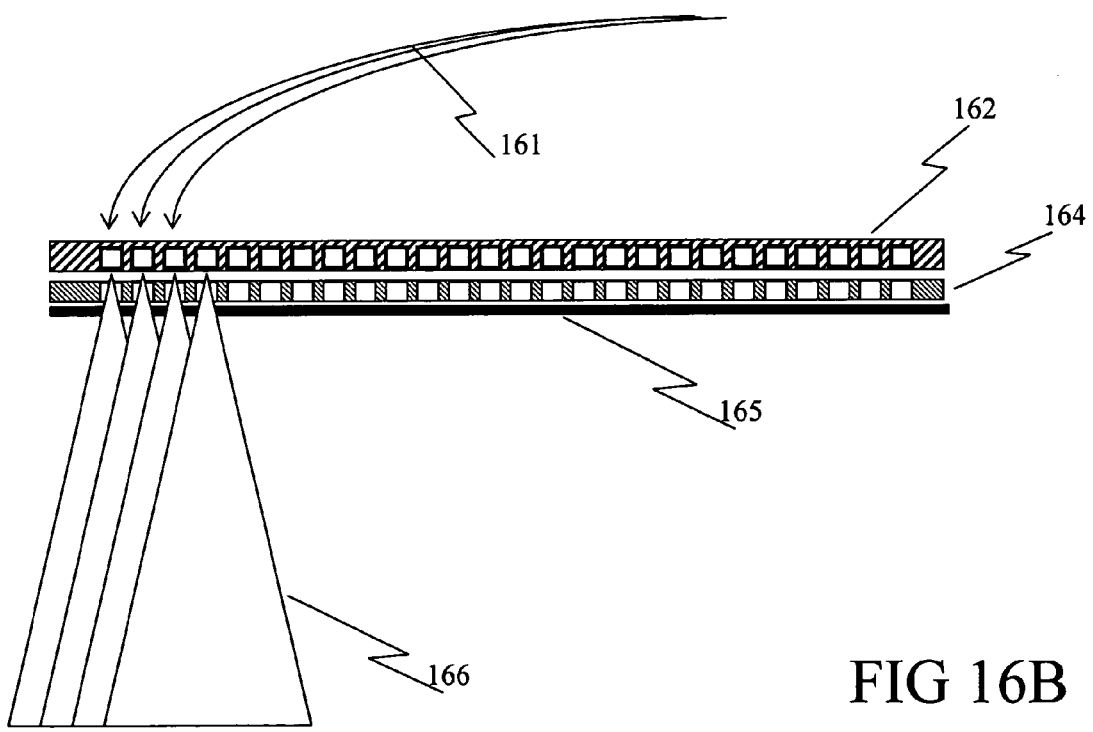

As noted a requirement of the system is that a larger number of translated beams overlap in increasing, known, and controllable amounts from a given beam direction as the beams penetrate deeper in tissue. It is also possible to deliver indexed beams of radiation that meet these requirements by other means. For instance, instead of attaching the x-ray tube to a robotic arm and using the robot to index the tube, the tube could be held still and the patient support device indexed. Another means for realizing the same goal FIG. 16 is to use a scanning electron beam device that scans a small electron beam 161 over an anode target in a predetermined pattern. The anode target has an at least a one-dimensional array of equally spaced targets 162 dispersed over its solid surface 163. When the electron beam hits the target photons are generated. On the under side of the plate is adhered 164 a secondary plate of beam blocking material that has at least a one-dimensional array of equally spaced apertures acting as x-ray transmissive passages through the collimator corresponding in position to the targets 162. On the underside of the secondary plate 84 can be a tertiary plate made of attenuation material 165. Each of the apertures is precision shaped such that a beam emitting from the target lying over the aperture is collimated to create a beam 166 that spreads as it leaves the plate. By controlling the thickness of the collimation plate and the shape of the hole, a pattern of beam overlaps can be created that is the same as would be produced by the preferred embodiment described above. This entire apparatus can be secured to the end of a robot arm or c-arm or other positioning device so that it can be brought to overlie closely the tissue surface to be treated.

Surface Guide for Implementing Array

Figure 17A:
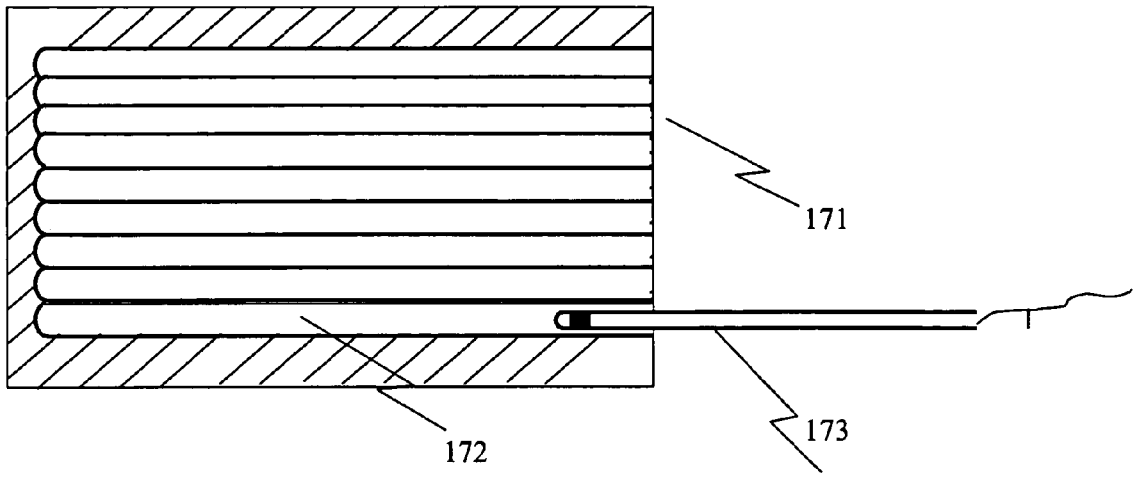
FIG. 17A to 17B shows two views of an alternative means for producing indexed beams of radiation used to treat the surface of a patient or cavity.
Figure 17B:
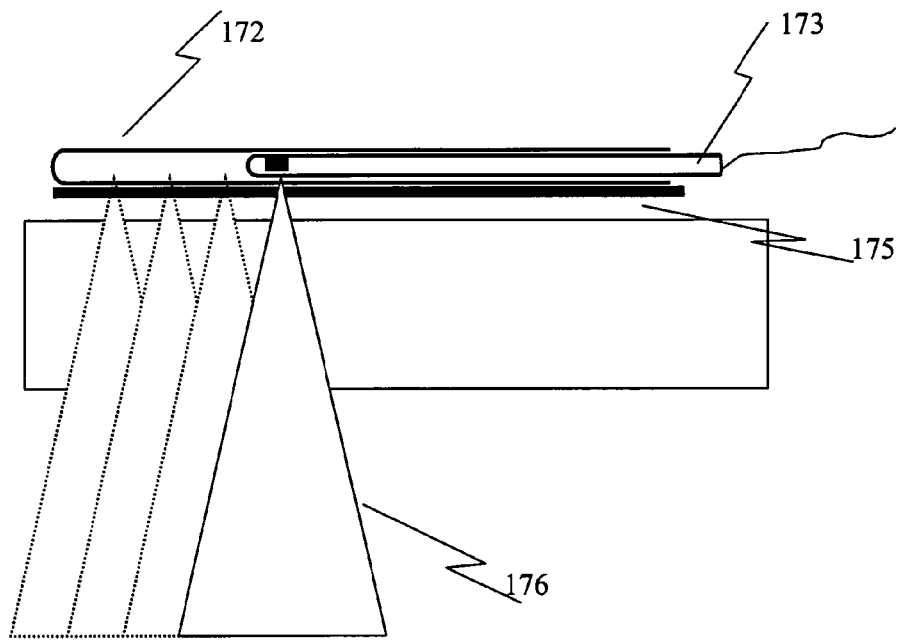

An additional means for delivering precisely the indexed position of the beams would include establishing a predetermined path laid down for a radiation delivering catheter to follow that involves effectively creating variable indexing of catheter position in at least two directions or multiple catheters in at least one direction and where means are provided for varying beam spread and beam attenuation. For instance, in FIG. 17 a grid 171 of tubes or channels 172 is created into which the radiation device 173 can be inserted. Each tube or channel is keyed to the catheter containing the radiation device such that the device can be inserted into the channel in a known orientation that is constant from channel to channel or tube to tube. The radiation tube can be indexed along the length of the guide tube 172 using the robot or some other linear indexing device such as a remote afterloading device used commonly with high dose radioactive sources or with commercial electronic x-ray tubes. Under the grid is placed a pad 175 made up of attenuation material through which the beams will pass. In this application, the x-ray tube or radioactive source will need to be configured to shape the beam 176 through the use of a radiolucent window or specifically constructed photon target, and the indexing in the direction perpendicular to the length of the guide tube will be predefined by the position of the guide tubes. Alternatively, a collimation plate can be laid on the tissue surface that has in it at least one dimensional array of apertures that can be used to collimate the beam to meet the shape and index required to produce the desired dose distribution. In such an implementation, the device used to establish the path of the radiation source would have shielding material surrounding it in all areas except the portion that comes in contact with the tissue surface. In this manner collimated beams would be delivered to the tissue while the rest of the patient or room in which the patient was being treated would be shielded from radiation.

Collimation System

Figure 23A:
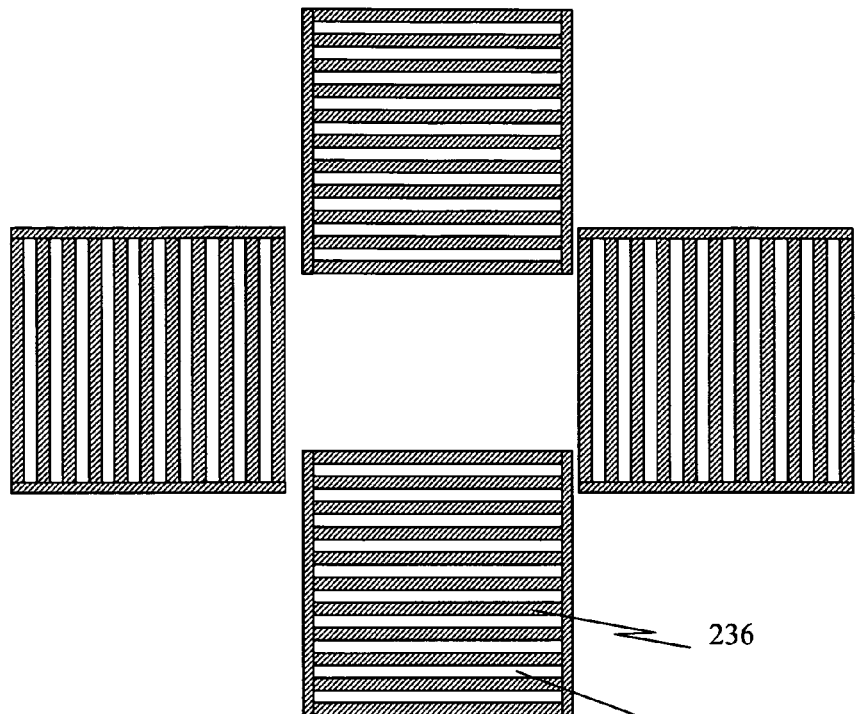
FIGS. 23A, 23B and 23C shows a mean for variable collimating an array of treatment beams.
Figure 23B:
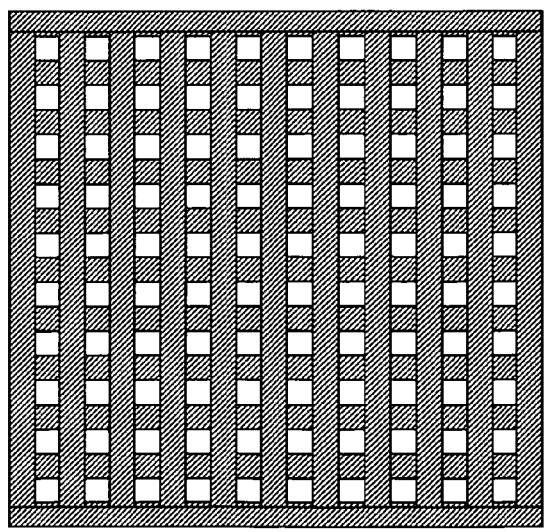
Figure 23C:
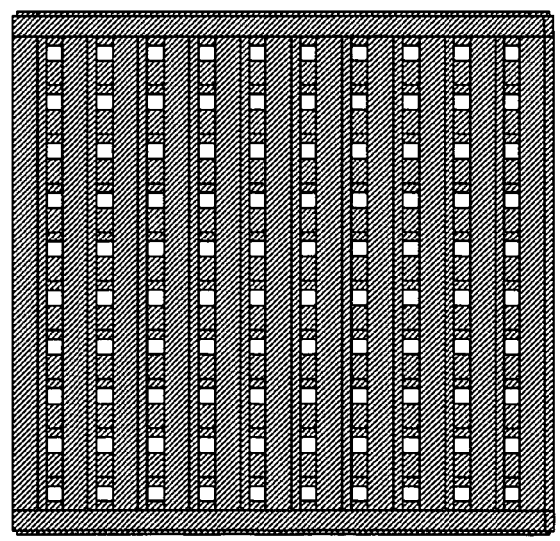

A collimation system FIG. 23A-FIG. 23C has been designed for use with both of these alternate embodiments. It comprises four plates of similar shape and design shown in FIG. 23A each of a thickness and material appropriate for blocking the radiation beam by greater than 98%. Ideally the plates are constructed of a very radiodense material such as tungsten in order to keep the overall thickness of the collimation to as small an amount as possible. Each plate comprises a lattice with a series of strips of beam blocking material 236 alternating with strips of no material 237. These plates are overlaid on top of each other in a stacked fashion, two of the plates orthogonal to the other two, such that an at least one dimensional grid of transmissive openings are created FIG. 23B. The size of the openings can be varied in a continuous fashion by moving all four plates in by the same amount. This will cause a uniform and equal decrease in the size of all of the openings as in FIG. 23C. Any means for driving the plates the appropriate distance can be used.

Planning System and Target Definition

The determination of beam index is the most important determinant of modifying the depth dose curves. Although the use of variable attenuation and beam shaping is of significant value, it is possible to benefit just from the ability to precisely implement a predetermined but variable index amount, or any other combination of variable index and one or more of beam energy, beam attenuation, and beam blocking.

As indicated, there can be quite a few variables that will affect the resultant dose distribution, including but not limited to beam divergence, beam attenuation, beam energy, and beam indexing. These variables must be factored into the treatment planning process. It is desirable that this planning process be automatic as possible and as fully integrated into the delivery system as possible. Therefore the preferred embodiment includes also a means for generating a treatment plan that will result in the correct dose delivery. Since as shown the depth dose curve is sensitive to the amount of attenuation, beam spread, and beam index, the planning system must be able to determine the correct combination of values that will result in the desired depth dose curve. In addition, the system must know what is the size and shape of the region to be treated.

Figure 18:
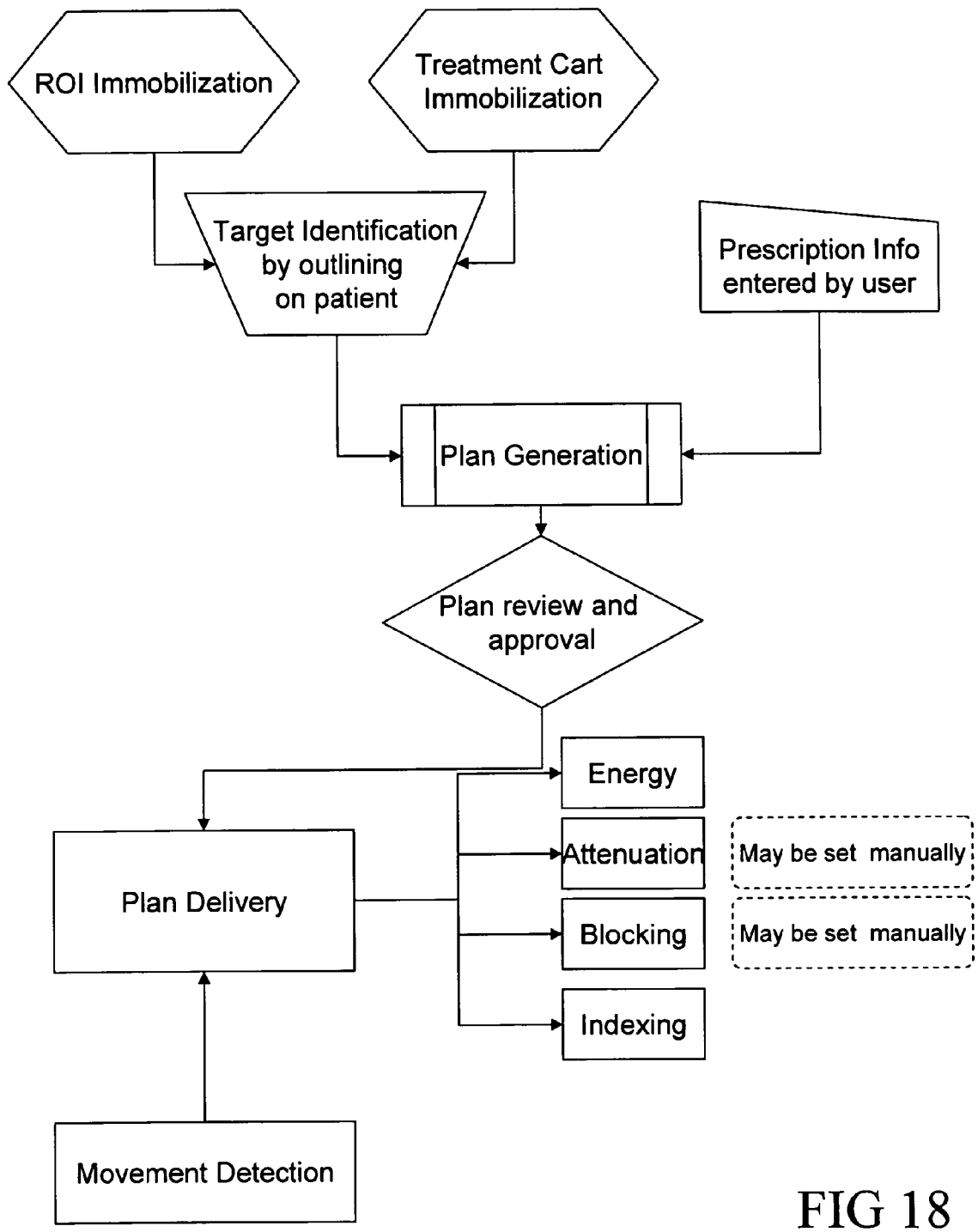
FIG. 18 shows the flow diagram for using this invention.

The planning flow is diagramed in FIG. 18. The first step, after immobilizing the region to be treated as well as the delivery device, is to identify and delineate the region to be treated. The region can be on or below the surface of the patient, in a cavity and underlying region created following a surgical resection, on or below the surface of an internal cavity, hollow viscus, or lumen, or deep in tissue surrounding an inserted probe or conduit or catheter. The preferred embodiment for this step of the process calls for acquiring directly off the patient the shape and location of the region to be treated. This can be done by tracing, outlining, or painting over the area to be treated with a localization system that then transfers this information to the planning system. In the preferred embodiment the robot, or a multiple degree of freedom device, that will be used to guide the delivery of the treatment is used to acquire information directly from the patient regarding the region to be treated. After immobilizing the patient and the robot next to the patient, the robot is used in a passive data acquisition mode whereby the control system for the robot records the position of the tip of the arm in the coordinate system of the robot as the user guides the robot arm around the contour of the region to be treated or over the surface of the region as if painting it with a paint brush. That is, the user traces the region to be treated with the arm of the robot while the control system records the movement of the arm and computes the location of the tip of the arm as it is moving. This "recording" capability is common to many existent robot systems. Functionally, at the time of treatment, the control system is put into a "data acquisition" mode, which automatically places the arm into this passive mode, and the region to be treated is outlined by the user tracing it or "painting over it" with the end of the arm. Although it is preferred that the device used to treat the patient is the same device used to acquire information about the region to be treated, it is possible to separate these two tasks. Thus another means of acquiring the same data is to use the cameras 191 of a camera localization system FIG. 19 to determine the position of active or passive markers 192 placed on the robot arm or on a pen that is used by the user to trace the region of interest 195 in a plane perpendicular to the region 193 in FIG. 19A and looking down on the region 194 in FIG. 19B. A magnetic localization system also could be used in place of the camera system as could any other means for acquiring 3-D data such as but not limited to a an infrared localization system, a sound-based localization system, a laser scanning system, or a laser range finder system.

This 3-D information designating the spatial limits of the region to be treated is transferred automatically to the treatment planning system for plan generation as in FIG. 18. The depth and thickness of the region to be treated is designated by the user by entering the appropriate values into the user interface of the planning system or by manipulating a small graphic tool 201 in FIG. 20A displayed on a screen of the user interface 200 of the planning system; the user both moves the tool around on the display to define depth of desired dose (distance below the surface) and adjusts the size of the tool to indicate thickness of region to be treated. This allows the user to define a range of sizes and regions to be treated, such as 204 a thin lesion at the surface, 205 a thin lesion below the surface, and 206 a thick lesion below the surface. These two pieces of data, along with the shape and size and location of the region to be treated, as well as the desired dose to which it should be treated, also entered by the user, are used by the on-board planning system to generate a treatment plan. The plan will determine automatically the best combination of index amount and dwell time at each beam position, as well as beam energy, attenuation, and beam shape if the delivery device can support these features, to achieve the desired treatment as according the flow in FIG. 18. Any number of algorithms can be used to generate the treatment plan based upon the entered data and the known effect the various variables have on the shape of the depth dose curves; this process is well known in the field of radiation therapy and is known as inverse treatment planning. Of course it is also possible to determine the treatment delivery parameters by hand or in a manual "trial and error" process as is the case with many approaches to treatment planning.

As noted, the planning process results in a set of delivery parameters that includes at least beam positions and beam position dwell time and can include the energy, attenuation factor, and beam shape. After reviewing the plan, the user approves the plan and then initiates treatment. This sets the robot into delivery mode, selects the degree of attenuation, energy, and beam shaping if such features are supported, and activates the x-ray tube. The robot then proceeds to deliver the treatment under computer control until the entire target is treated to the desired dose.

Treatment Monitoring

It is also possible to include the ability to terminate the treatment should the patient move during administration of the radiation as indicated in the flowchart. Typically, prior to initiation of the treatment process, the region to be treated will be immobilized by one of any number of such devices currently used in radiation therapy or that are developed specifically for the region in question. However, even following such immobilization, it is possible for the patient to move or to move the portion of their anatomy in which the treatment region lies. If such should occur while the treatment is underway, an incorrect dose might be delivered to the region being treated as well as to regions that are not to be treated.

The disclosed device can include any number of means for monitoring patient movement during the course of treatment in order to ensure that the treatment is not delivered to an incorrect location as shown in FIG. 21. One embodiment comprises an x-ray sensitive plate such as an amorphous silicon panel 210 or other means for recording the passage of radiation positioned under the region to be treated 211 that is monitored in real time by a control system. On the underside or back of the region to be treated are placed several small radiopaque markers 212 or an array of markers or patterned marker system such as a diverging triangle with radiopaque legs or a simple grid of radiopaque lines 213. At the time that the surface is "traced" or scanned by the robot system 214, a small amount of low energy radiation 215 can be used to take a continuous set of "images" of the markers, each of which correlates to the recorded position of the robot relative to the markers at the time the image are taken. At the time of treatment, an additional series of continuous images can be taken of the markers for each indexed position of the robot arm. The control system can correlate the position of the markers on the treatment images to the position of the markers on the localizing images for a given position of the robot. If the positions are the same the treatment is allowed to continue. If the positions are different, then that implies that the treatment region has moved.

The robot can be used in another fashion to determine movement prior to the start of treatment but not during treatment. At the time of region identification (time1) and prior to start of treatment (time2), the user can manually identify marks on the region surface or markers placed on the region surface. If the position of these marks or markers has changed between time1 and time2, then movement has occurred.

Other methods for accomplishing the same include the use of a localization system to track markers placed on the tissue surface in the vicinity of the region being treated. The location of the markers determined at the time of region identification is used as a baseline. At the start of and during treatment the position of the markers are determined continuously or intermittently and compared to the baseline position in order to determine if movement, and how much movement, has occurred. For instance, cameras 226 can be used that monitor passive or active markers 227 secured to the patient surface near the region being treated. A magnetic localization system also could be used in place of the camera system as could any other means for acquiring the 3-D position of markers affixed to the region being treated such as but not limited to an infrared localization system, a sound-based localization system, and a laser range finder system. Another means of accomplishing the same involves using a laser scanning device to scan the region in question. Following an initial scan that acts as a baseline, subsequent scans generated during the course of treatment can be compared to the baseline image in order to determine if movement has occurred.

As an additional means of determining if movement has occurred between the time of region identification and the start of treatment, it is possible to use the robot to retrace the region, or to identify specific portions of the region, or marks places on the patient at the time of region identification that are identified initially at the time of region identification, before treatment begins. The new data is compared to the data acquired at the time of region identification in order to determine if movement has occurred between the time of region identification and the start of treatment.

An indication by any of these means that the patient has moved can cause the control system to shut down the treatment. Alternatively, the system can continue the treatment while compensating for movement by determining the vector and amount of movement and changing the delivery instructions for the delivery device such as a robot so that it positions the delivery arm correctly for the new position of the patient. In most cases the movement will be small and can be corrected in this manner. If the movement is outside the ability of the system to correct, such as if the patient gets up off the treatment table or if the patient lifts an arm undergoing treatment off of the table, the treatment can be terminated until corrections are made.

Targets Distance from Delivery Device

Although the methods and apparatus described so far will increase significantly the dose at depth compared to the dose at the tissue surface, this increase may not be great enough to treat targets located deep to the tissue surface that are not targeted directly by a needle but treated instead by an external approach. At a typical deep target depth of 10-30 cm, the residual dose to a 4 cm target volume from an unmodified low energy x-ray source will be on the order of 0.001-0.1% of the dose at the tissue surface (assuming a half-value layer in tissue for a 50-70 kvp beam of 2 cm). Using the techniques described above, the residual dose to a 4 cm target at a target depth of 10-30 cm can be increased to as much as several percent. This obviously is not enough to allow the treatment of such deep lesions.

2-D Array

It is possible however to furthermore enhance the methods and apparatus herein described such that it can be used to treat such deep lesions. The first step in so doing is to increase the actual dose delivered by the apparatus itself while reducing surrounding dose. This invention includes several means for achieving said increase, as applied to the preferred embodiment using the scanning electron apparatus described previously and illustrated in FIG. 16A-B, although other of the means described herein can be used as well, specifically the embodiment employing a single or plurality of small x-ray sources used to create a 2-D array of beam emitters. However, it is required that an effective two-dimensional array of beams be used to treat the patient; this will increase significantly the number of beams that hits the target thereby increasing dose.

Convergent Beam Delivery

Figure 24A:
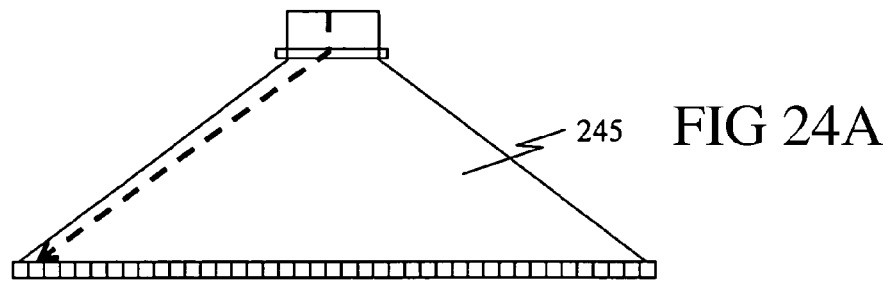
FIGS. 24A, 24B, 24C, 24D and 24E shows parallel and convergent delivery geometries as applied to a scanning electron beam device.
Figure 24B:
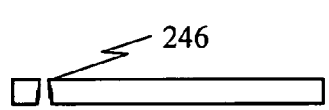
Figure 24C:
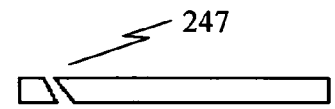
Figures 24D, 24E:
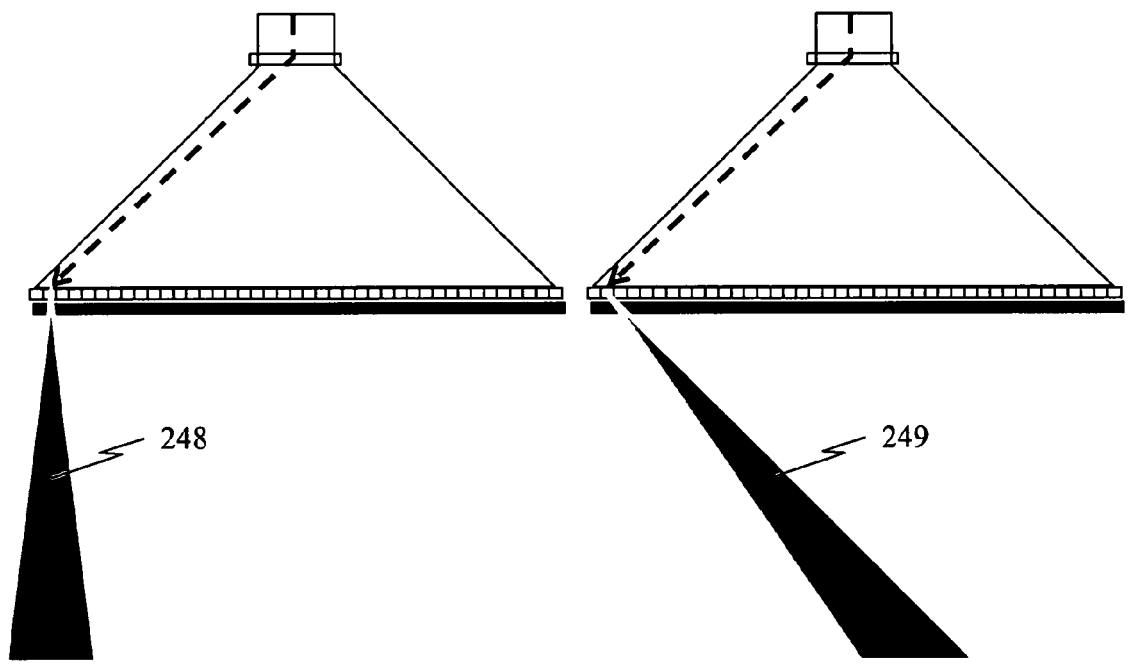

A second means changes the delivery geometry of the treatment. Element 246 in FIG. 24B illustrates the parallel geometry applied to a collimator that would be part of an electron-delivery device 245 in FIG. 24A as described previously in FIG. 10A-10C; FIG. 24D element 248 shows the beam that would result from such a collimator. In the following additional embodiment, the geometry is changed to one that is convergent, using a collimator 247 in FIG. 24C generating beam 249 as depicted in FIG. 24E. The major benefit of a convergent set of beams rather than a parallel set of beams is that more of the dose is restricted to the desired region of tissue. This results in the dose to nontarget tissue being lower than would be possible with a parallel beam arrangement. In order for all beams to converge on a target at depth, each hole in the collimator plate must be formed to generate different shaped and directed beams of radiation, such as beams 251-253 in FIGS. 25A, 25B and 25C. However, each beam of radiation still passes through a unique section of tissue surface. In addition, there must be a different set of radiation transmissive passages for targets of different sizes, such as a small target 254 in FIG. 25E and a larger target 255 in FIG. 25G. Note that the collimator plates 256 for the small target in FIGS. 25D and 257 for the large target in FIG. 25F have a different orientation and shape to each transmissive passage through the collimator plate.

Figure 26A:
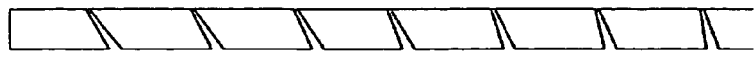
FIGS. 26A, 26B, 26C and 26D shows using a parallel plate design to deliver convergent beams.
Figure 26B:
Figure 26C:
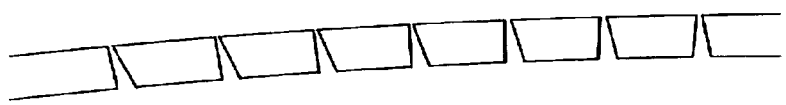
Figure 26D:
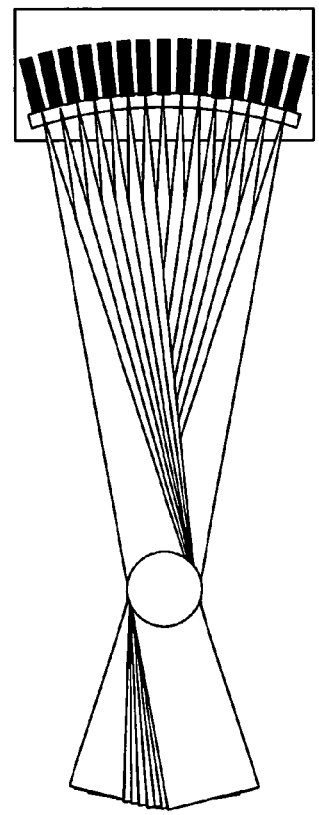

Assuming that target volumes are always treated at a given depth relative to the beam generation device itself, an approach that is standard practice in radiation therapy, it is possible to manufacture a series of collimator plates with each one used to create a specific size target at a given depth. However, since the size of targets that need to be treated can vary over a large range, from under 1 cm to as large as 10 cm or more, this will require a very large number of plates or a very coarse resolution in terms of the sizes of volumes that have a collimator appropriate to their size. Therefore herein is disclosed a means for using a single collimator system with transmissive passages all formed in the shape and orientation such that a convergent beam geometry will result for a range of target volumes. FIG. 26A describes a one-dimensional version of a two dimensional collimator plate geometry with each transmissive passage of a different shape and orientation such that all beams will converge at a specific depth SAD. FIG. 26B describes a similar collimator plate but with each passage of the same shape and orientation. By taking the collimator plate in FIG. 26B and bending it so that it follows the surface of a sphere of a radius equal to the same depth SAD, all beams will be made to converge as in FIG. 26C but will be generated by a collimator plate where the transmissive passages are manufactured so that they are initially parallel. Beam size adjustment with infinite resolution can now be achieved by applying this concept to the collimation system described in FIG. 23, as now depicted in FIG. 27. Four identical plates 274-277 are arranged in pairs, 275/277 and 274/276, that are orthogonal to each other; to adjust the size of all of the transmissive passages simultaneously each plate is slid along its descriptive arc instead of along a flat plane as in FIG. 23.

As presented previously, the dose at a depth of 10 cm from a single beam of heavily filtered low energy radiation, say 50-120 kvp, will be approximately 3-20% of the dose at the skin surface; at 30 cm this will be reduced to 0.001-0.4%.

TABLE 1

Approximate DD for Various HVL

| | % DOSE for HVL | | | |
|---|---|---|---|---|
| DEPTH (cm) | 2 | 2.5 | 3 | 4 |
| 0 | 100.0 | 100.0 | 100.0 | 100.0 |
| 5 | 10.0 | 12.5 | 20.0 | 40.0 |
| 10 | 3.0 | 6.3 | 10.0 | 22.0 |
| 15 | 0.5 | 1.6 | 3.0 | 7.0 |
| 22 | 0.1 | 0.2 | 0.7 | 2.0 |
| 30 | 0.0 | 0.0 | 0.1 | 0.5 |

Figure 28A:
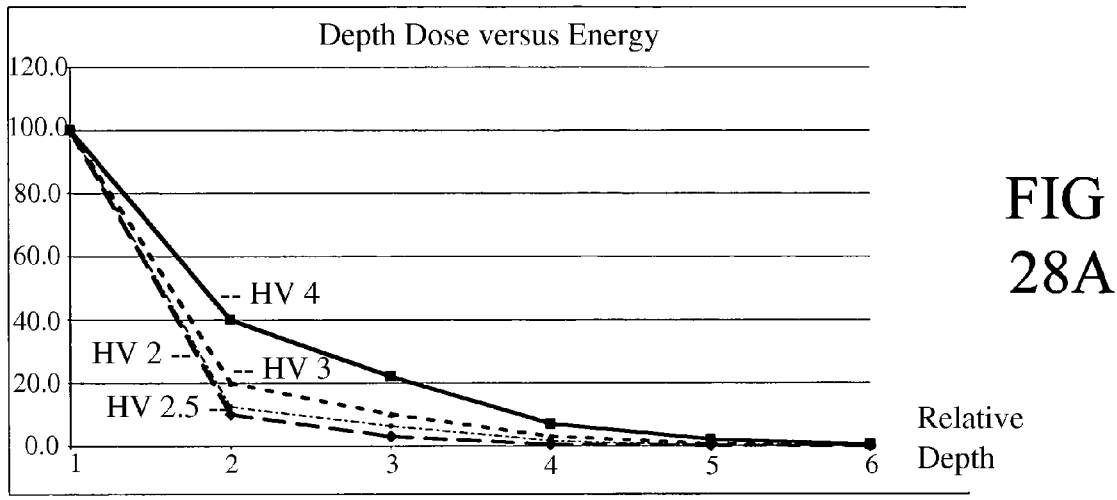
FIGS. 28A, 28B and 28C shows depth dose curves for different half-value layers for different delivery scenarios.

This is shown in FIG. 28. In FIG. 28A, the normal depth dose curves for a range of beam energies are shown; each curve is the depth dose for an energy with a half value layers (HVL) ranging from 2 to 4 (equivalent to a range of energy of from approximately 50-120 k; the greater the beam energy the greater the half value layer), given as percent dose versus relative depth (in this case depth ranges from 0 to 30 CM depth in tissue).

Energy Modulation

Figure 28B:
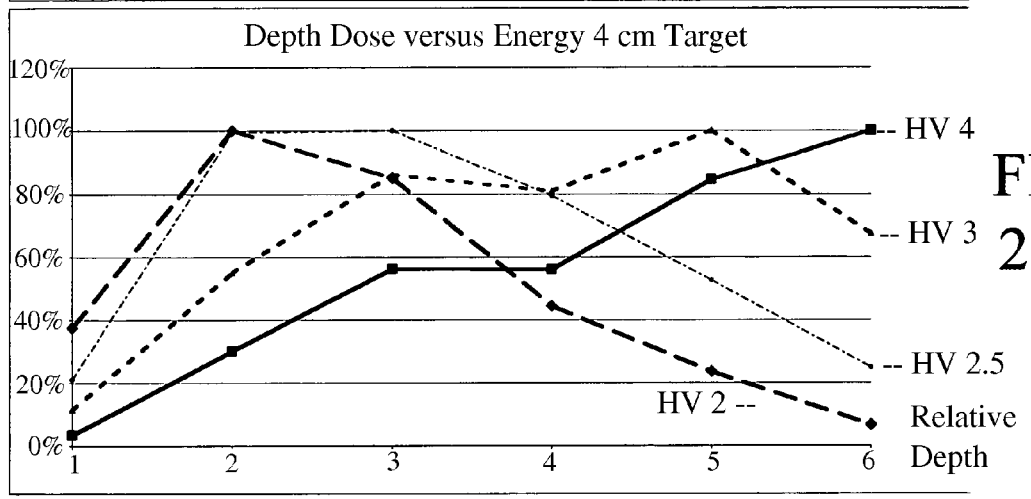
Figure 28C:
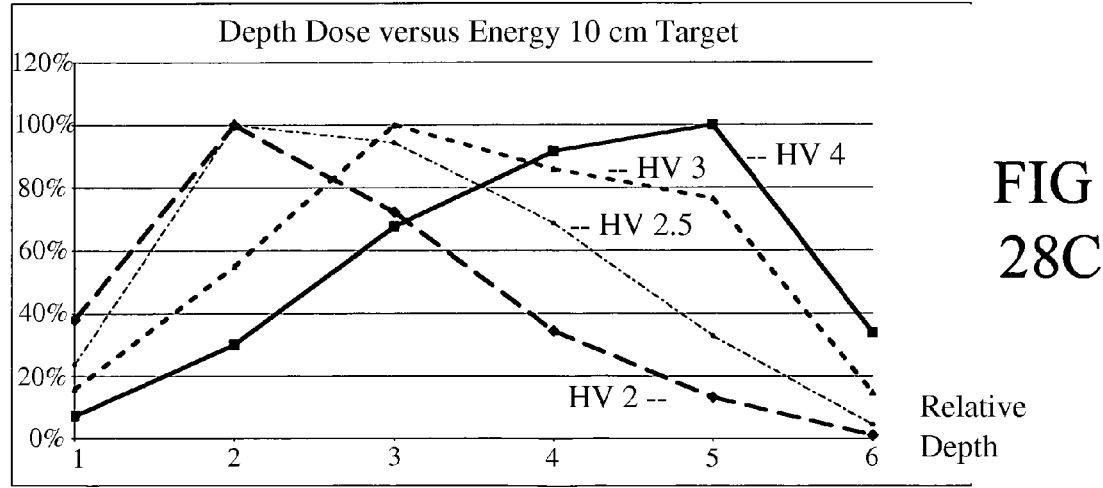

A typical scanning electron beam delivery system as described herein will generate 10,000 or more effective beams of radiation evenly spaced that will converge on the target volume thereby increasing the dose at depth significantly. However, the increase in dose at depth is not a factor of 10,000 because some of these beams will begin to overlap outside the target volume, the number increasing as the depth of the target decreases (assuming a fixed focal length for beam convergence). Beams will overlap to a greater and greater degree as they transverse tissue on their way to the target. At the same time, the depth dose for each beam will decrease due to tissue attenuation. Thus the actual increase in effective dose will depend on the delivery geometry, the size of the target, and the beam energy. The depth dose curves for the same HVL but using the herein described methods and apparatus for converging the beams at depth are shown in FIG. 28B as applied to a 4 cm target and FIG. 28C as applied to a 10 cm target. The focal distance for beam convergence is kept at a constant 30 cm for all deliveries. The related values in tabular form are presented in Table 2 for a 4 cm target 30 cm deep and in Table 3 for a 10 cm target.

Figure 29A:
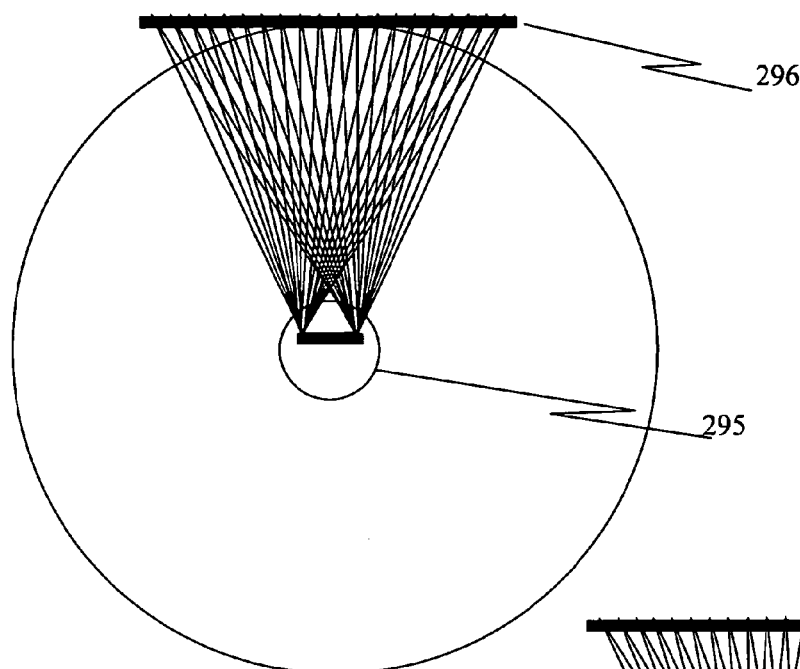
FIG. 29A to FIG. 29B shows varying depth of treatment by varying position of beam array.
Figure 29B:
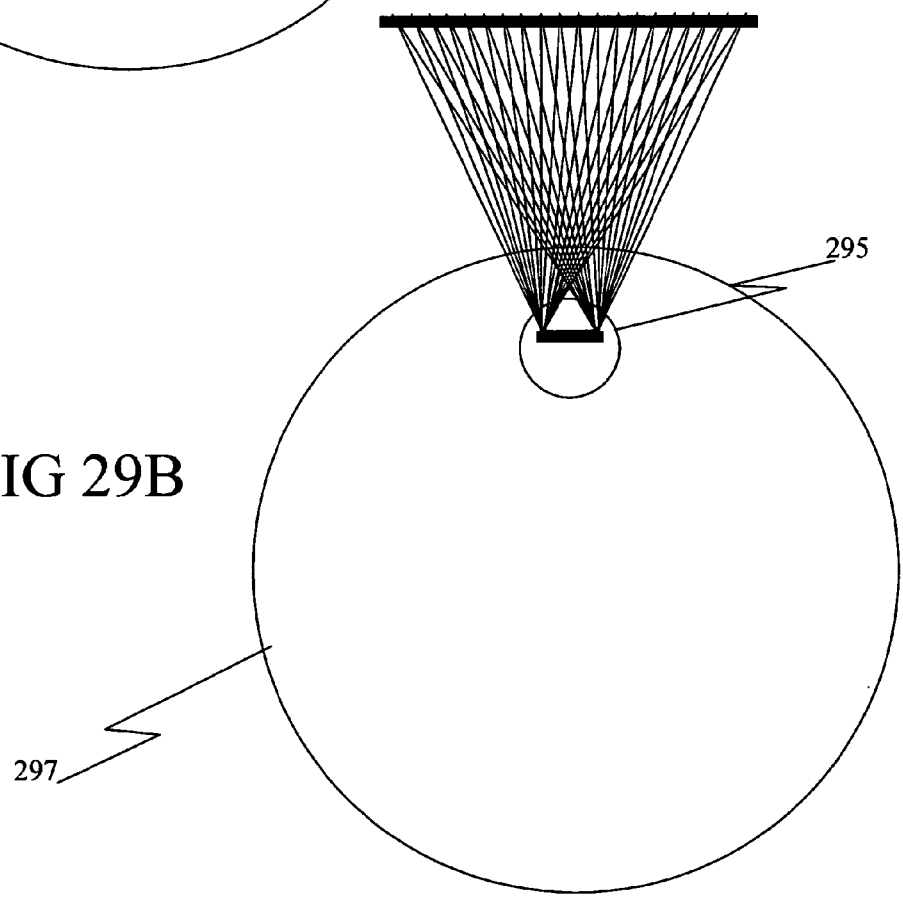

These are believed to be representative values for the technique described and are not actual or measured values. Note that in both of these cases the maximum dose moves deeper in tissue as the half-value layer or energy increases. Thus it is possible to vary the depth at which the maximum dose will be delivered merely by changing beam energy while leaving focal depth and depth in tissue the same. That is, in FIG. 29 if using an array 296 of beams to treat the target volume 295 located at 10 cm in patient 297, rather than changing the delivery geometry from a focal point 30 cm deep in tissue as in FIG. 29A to one that is 10 cm deep in tissue as in FIG. 29B, the geometry can be left untouched with only the energy being changed—this will move the point of maximum dose to a more shallow point in tissue as in Table 3.

TABLE 2

Approximate DD for HVLs Using Disclosure 4 cm Target

| | % DOSE for HVL | | | |
| --- | --- | --- | --- | --- |
| DEPTH (cm) | 2 | 2.5 | 3 | 4 |
| 0 | 38% | 21% | 11% | 3% |
| 5 | 100% | 99% | 55% | 30% |
| 10 | 85% | 100% | 86% | 56% |
| 15 | 44% | 80% | 81% | 56% |
| 22 | 24% | 53% | 100% | 85% |
| 30 | 7% | 25% | 68% | 100% |

TABLE 3

Approximate DD for HVLs Using Disclosure 10 cm Target

| | % DOSE for HVL | | | |
| --- | --- | --- | --- | --- |
| DEPTH (cm) | 2 | 2.5 | 3 | 4 |
| 0 | 38% | 24% | 16% | 7% |
| 5 | 100% | 100% | 55% | 30% |
| 10 | 72% | 94% | 100% | 68% |
| 15 | 34% | 69% | 86% | 92% |
| 22 | 13% | 33% | 77% | 100% |
| 30 | 1% | 4% | 15% | 34% |

Multiple Field Treatment

Figure 30A:
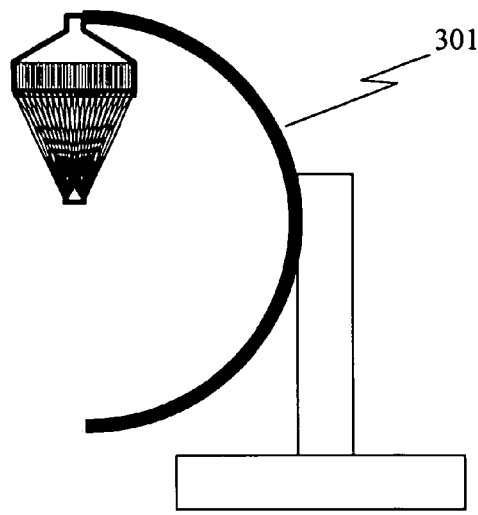
FIG. 30A, FIG. 30B and FIG. 30C shows the delivery of multiple fields spaced around a patient.
Figure 30B:
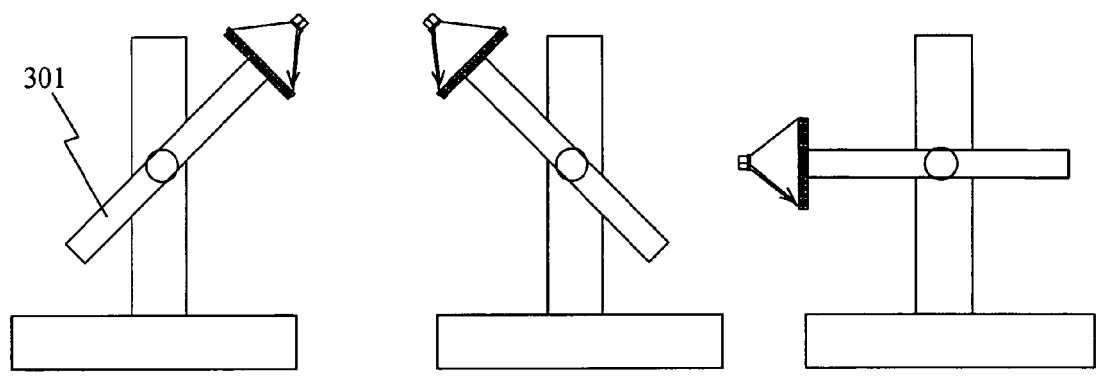
Figure 30C:
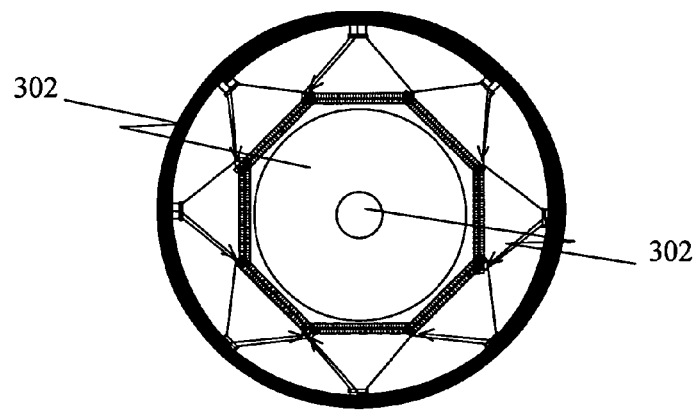
Figure 31:
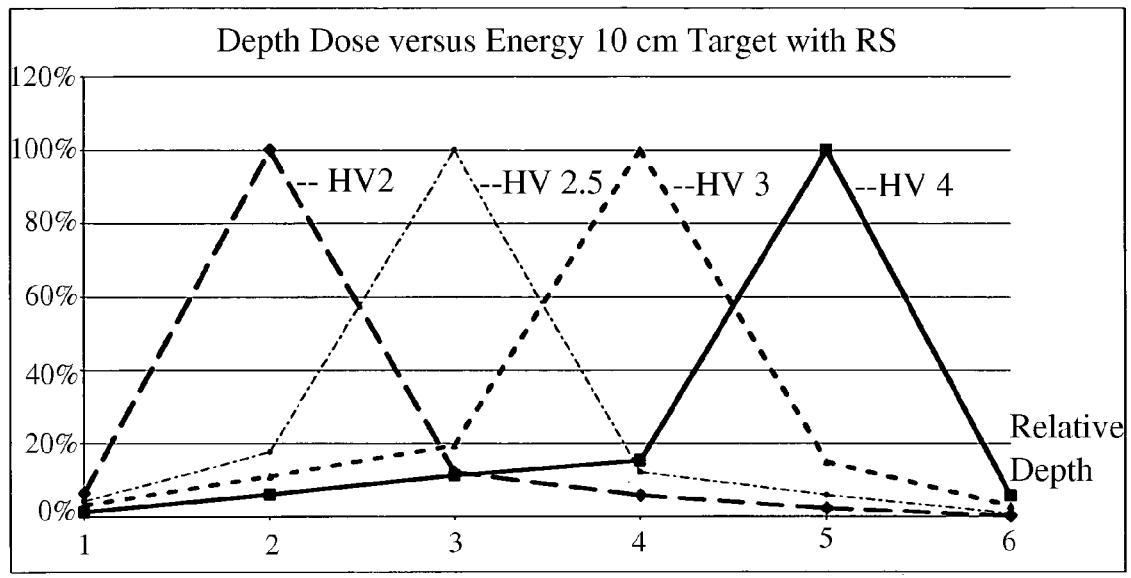
FIG. 31 shows depth dose curves using multiple fields with the current invention.

Even with this approach, the dose at depth is only increased to a therapeutic ratio of about 1:1. A second means and apparatus will improve even further the dose at depth relative to anywhere else while reducing even further dose to surrounding tissue as well as the surface dose. The scanning electron radiation device, or other embodiments as described previously herein, can be secured to a c-arm or similar device 301 in FIG. 30A-B that is used to position the array at a plurality of positions, defined as multiple fields (MF) as in FIG. 30B distributed around the patient 303 in FIG. 30C with the delivered fields of radiation converging on the target volume 302. As is the case with most rotational techniques, this will concentrate a greater number of beams on the target tissue and not on nontarget tissue. By picking a number of fields appropriate to the size and location of the target, dose at depth can be increased significantly. For instance, by using six fields evenly spaced for a 10 cm target the related values would be as in Table 4 and FIG. 31.

TABLE 4

Approximate DD for HVLs Using Disclosure 10 cm Target Multiple Fields

| | % DOSE for HVL | | | |
| --- | --- | --- | --- | --- |
| DEPTH (cm) | 2 | 2.5 | 3 | 4 |
| 0 | 6% | 4% | 3% | 1% |
| 5 | 100% | 18% | 11% | 6% |
| 10 | 12% | 100% | 19% | 11% |
| 15 | 6% | 12% | 100% | 15% |
| 22 | 2% | 6% | 15% | 100% |
| 30 | 0% | 1% | 3% | 6% |

Dose Enhancement

This improvement in therapeutic ratio, roughly equal to the number of fields used, although quite significant, may be enough for a fractionated treatment but may be not enough to deliver the dose required for killing all malignant cells, believed to be in excess of 25-50 Gy in a single fraction, without damaging normal tissue (believed to be 5 Gy maximum tolerated dose in a single fraction but ideally less than 2 Gy). This is especially the case if a number of large doses are to be used in order to deal with the problem of radioresistant cells in the center of a target volume. In this case, it would be ideal to deliver a large tumorcidal dose in one fraction to the radiosensitive cells that are oxygenated, then after they die and the inner cells are oxygenated, deliver another large tumorcidal dose, repeating this process as many times as is required in order to kill all cells once they are oxygenated.

However, the ability to get a sizeable dose at depth from low energy x-rays in the range of 50-120 or more kvp makes it possible to benefit from the practice of dose enhancement in order to improve even further the therapeutic ratio. Dose enhancement (DE) occurs if radiation is delivered to an interface between normal tissue and a high z material. A photon, of an energy near the absorption energy of an inner electron shell in the target material, transfers its entire energy to the electron that subsequently is ejected from the atom (photoelectron). The relatively low kinetic energy of the ejected photoelectron is equal to the incident X-ray photon energy minus the binding energy of the electron. The vacancy in the electron orbital resulting from the electron ejection is filled by an electron from an outer orbit (with a lower binding energy), leaving a vacancy in this outer orbit that in turn is filled by another electron from an orbit even further away from the nucleus. The surplus energy liberated when an electron drops from an outer shell to a shell closer to the nucleus results either in the emission of a fluorescent photon or in the ejection of an additional secondary electron (Auger electron) from the same shell. If Auger electron emission occurs, the atom is left in a doubly ionized state (due to two ejected electrons) that is resolved by the dropping of other electrons from outer shells to fill the holes. This cascade process results in the release of a large number of very low energy electrons that travel very short distances and deposit their energy (track ends) locally (therefore with a very high linear energy transfer (LET)). If the electrons are produced near the DNA they can be very effective in killing the cell through double strand breaks.

The depth of penetration of Auger electrons is very small, on the order of 1-10 micrometers. Thus reliable cell death requires that the Auger electron be generated within 1-10 micrometers of the DNA, e.g. within the cell (and preferably within the nucleus) itself. The disadvantage of this approach is that the process for generating the Auger electrons must take place within the cell. The advantage is that the tumorcidal effect of the radiation is limited to the target cells. As a result, such a therapy has the potential for repetitive dosing with minimal toxicity.

Gold Nanoparticles

Figure 32A:
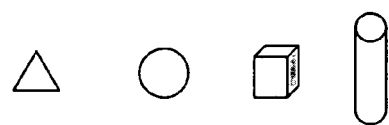
FIG. 32A, FIG. 32B and FIG. 32C shows multiple sizes, shapes, constructs of nanoparticles.
Figure 32B:
Figure 32C:

In the preferred embodiment gold nanoparticles are used in association with the scanning electron system delivering convergent beams of radiation of variable energy that have been filtered and collimated, although other high z materials, other size particles, and other means of delivering convergent beams of radiation can be used as well. These gold particles can be of any size (FIG. 32B) or shape (FIG. 32A) and can be solid, hollow, or consist of a gold shell surrounding a core of some other material such as silica or iron or some other material (FIG. 32C) or any other construct ranging in size from several nanometers to even microns or millimeters in size. The gold surface of the nanoparticles, be they solid or hollow, provides a simple chemistry for the self-assembly of polyethylene glycol, antibodies, dendrimers, amino acids, or other agents that allow the nanoparticles to accumulate in the vicinity of, or to attach directly to or in, or be preferentially taken up by, the targeted cells and not in the vicinity of, or attached directly to, or taken up preferentially by, or in normal cells. The nanoparticles and their carriers or attachments can be delivered by IV injection, injected directly into the region of the tumor, or sprayed directly onto the target (if accessible), and can accumulate in concentrations sufficient to blanket all cells in the target volume to some degree.

Dose enhancement secondary to the release of Auger electrons from gold particles or other metals will occur when using most energies in the kilovoltage or orthovoltage range. Experimental studies using gold foil have shown that gold particles, when exposed to heavily filtered 50-70 kvp x-rays, generate a dose enhancement factor believed to be in excess of 150; the use of heavily filtered 100-120 kvp x-rays results in a dose enhancement factor believed to be greater than 50; the amount of dose enhancement is dependent on the match between the energy of the radiation and the energy of K, L, and M electron shells of the particle being used. In practice, however, the amount of enhancement that will be achieved in normal clinical conditions is much less as a result of the limited concentration of particles that can be achieved in target tissues relative to a piece of gold foil and the reliability of delivering the particles to the target tissue. The actual dose enhancement factor is related to the fraction of mass of the gold in tissue. Realistic numbers for dose enhancement based on experimental studies are believed to be in the range of 2-10× for the lower energy range and 1.3 to 3× for the higher energy range depending on beam energy and tissue concentration.

Even this degree of enhancement may not be enough to generate a useful treatment paradigm at the depth at which many tumors occur when using unmodified or even heavily filtered low energy radiation. Assume the values presented previously for unmodified kvp depth doses—3-20% of the dose at 10 cm and at 30 cm 0.001-0.4%. Multiply these by the number of fields to be used—6—and the dose enhancement factor—ranging from 10 for the lowest energies to 3 for the highest. This results in a best dose of 200% at 10 cm depth and 10% at a 30 cm depth. Even if the dose enhancement were increased by a factor of two at high energies and twice the number of fields were used, the resultant dose at a 30 cm depth would still be less than 25%.

Convergent 2-D Array Delivery, Multiple Fields, and Dose Enhancement

Figure 33:
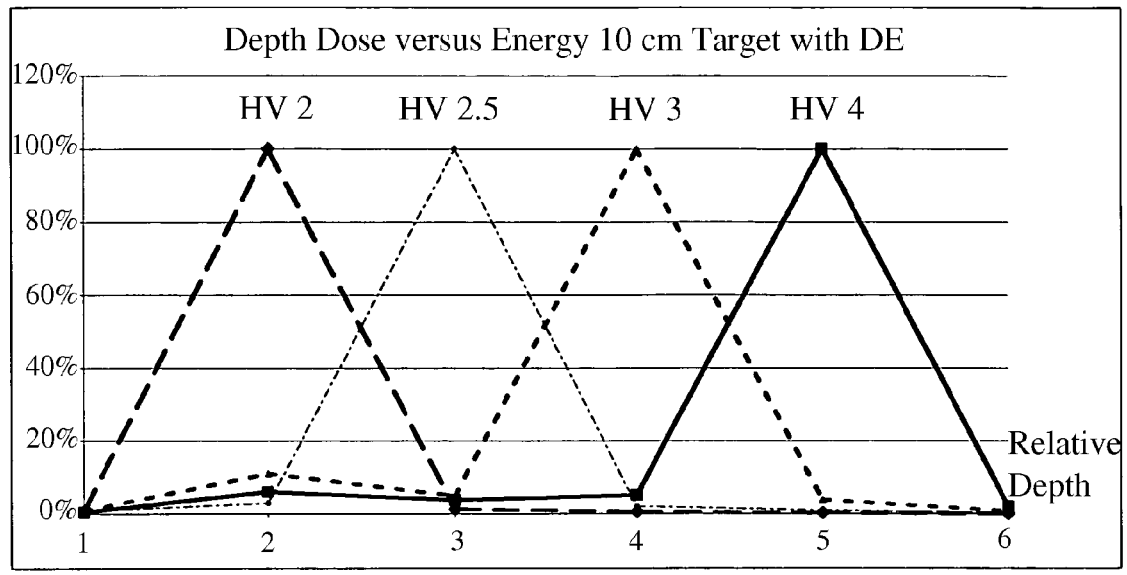
FIG. 33 shows depth dose curves using energy modulation to adjust for target depth coupled with dose enhancement and multiple fields with the current invention.

However, when the degree of dose enhancement achieved through the use of gold particles is coupled with the amount of dose that can be delivered to depth using the methods and means disclosed herein, a therapeutic dose can be achieved. Assume the values in Table 2 and Table 3 for 4 cm and 10 cm targets located at varying depth and use a combined "dose enhancement times multiple fields" factor of 12-60 for the lower energy ranges (3 to 10 DE times 6 fields) and 8-18 for the higher energies (1.3 to 3 DE times 6 fields). It thus becomes possible to deliver a dose to a target volume at a depth that will be greater by a factor of 20 or more compared to the dose delivered to the rest of tissue outside the treatment volume as shown in Table 5 and in FIG. 33. If higher energies are used a dose of a similar relative magnitude can be delivered to targets that are even 10 cm or greater in size at depths of 30 cm or greater; the dose enhancement effect is less but the dose delivered at depth by the techniques described herein is higher, thereby producing a greater effective dose at deeper depth.

TABLE 5

Approximate DD for HVLs Using Disclosure 10 cm Target MF & DE

| DEPTH (cm) | % DOSE for HVL | | | |
|---|---|---|---|---|
| | 2 | 2.5 | 3 | 4 |
| 0 | 1% | 1% | 1% | 0% |
| 5 | 100% | 3% | 3% | 2% |
| 10 | 1% | 100% | 5% | 4% |
| 15 | 1% | 2% | 100% | 5% |
| 22 | 0% | 1% | 4% | 100% |
| 30 | 0% | 0% | 1% | 2% |

Range Modulation

It is also possible to concentrate dose by keeping the focal distance the same while bringing the focal spot to overlap on the target volume by moving the delivery device farther away from the patient surface. This will increase the dose delivered to the target because of the maximum concentration of beams but will also increase the number of beams that cross at shallower depths, as shown in Table 6 for a 10 cm target, and therefore increase the dose at shallower depths (assumes a 30 cm focal spot, 10,000 beams total distributed equally from a delivery plate of 40 cm×40 cm converging on a 10 cm diameter target).

Figure 34:
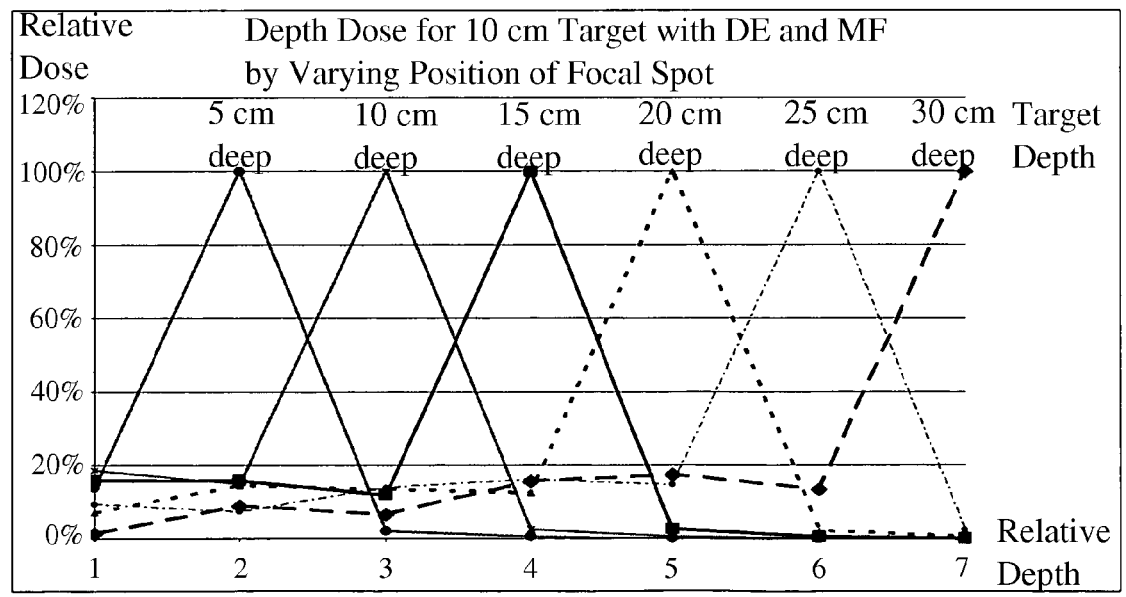
FIG. 34 shows depth dose curves using range modulation to adjust for target depth coupled with dose enhancement and multiple fields with the current invention.

However, the net result is the ability to position the location of maximum dose at the focal point, i.e. the target location, as can be seen in Table 7 as well as in FIG. 34. Thus it is possible to deliver serial radiosurgical or large single fraction doses (25-50 Gy) to kill malignant cells as they become oxygenated due to the death of surrounding cells since the dose to normal cells would be less than 2.5 Gy with one or both of the approaches.

Of course, different metals or high Z materials can be used in place of gold in the same manner as described above. The actual gain in therapeutic ratio would be determined by the maximum amount of dose enhancement, the amount of material in the tissues, and the % depth dose for a given metal and energy. However, the magnitude of the effects described herein will not be seen with energies in the MV range.

TABLE 6

Number of Beam Crossings with Varying Focal Spot Depth

| | NUMBER OF BEAMS CROSSING | | | | | |
|---|---|---|---|---|---|---|
| DEPTH (cm) | 30 cm | 25 cm | 20 cm | 15 cm | 10 cm | 5 cm |
| 0 | 11 | 200 | 400 | 2,000 | 5,000 | 10,000 |
| 5 | 200 | 400 | 2,000 | 5,000 | 10,000 | 10,000 |
| 10 | 400 | 2,000 | 5,000 | 10,000 | 10,000 | 10,000 |
| 15 | 2,000 | 5,000 | 10,000 | 10,000 | 10,000 | 5,000 |
| 20 | 5,000 | 10,000 | 10,000 | 10,000 | 5,000 | 2,000 |
| 25 | 10,000 | 10,000 | 10,000 | 5,000 | 2,000 | 400 |
| 30 | 10,000 | 10,000 | 5,000 | 2,000 | 400 | 200 |
| 35 | 10,000 | 5,000 | 2,000 | 400 | 200 | 11 |
| 40 | 5,000 | 2,000 | 400 | 200 | 11 | 0 |
| 45 | 2,000 | 400 | 200 | 11 | 0 | 0 |
| 50 | 400 | 200 | 11 | 0 | 0 | 0 |

TABLE 7

Approximate DD for 4 cm HVL with Varying Focal Spot Depth

| | % DOSE for Different Focal Depths | | | | | |
|---|---|---|---|---|---|---|
| DEPTH (cm) | 30 cm | 25 cm | 20 cm | 15 cm | 10 cm | 5 cm |
| 0 | 1% | 9% | 7% | 16% | 19% | 14% |
| 5 | 9% | 7% | 14% | 16% | 15% | 100% |
| 10 | 7% | 14% | 13% | 12% | 100% | 2% |
| 15 | 16% | 16% | 12% | 100% | 3% | 0% |
| 20 | 17% | 14% | 100% | 2% | 1% | 0% |
| 25 | 13% | 100% | 2% | 0% | 0% | 0% |
| 30 | 100% | 2% | 0% | 0% | 0% | 0% |

Targeting

Because the toxic effect of the treatment occurs only where the regions of metal or high Z nanoparticles and low dose radiation overlap, this approach is relatively insensitive to target volume movement during treatment. That is, as long as the radiated volume is large enough so that the cancer cells always lay within the radiated field, the cells will receive a lethal dose of radiation. Since the toxicity of the radiation alone can be kept relatively low (the lethal dose resulting from the combination of the delivered radiation times the enhancement factor), it does not matter if a somewhat increased volume of normal tissue is exposed to the radiation beam. This is in distinct contrast to typical radiation therapy, where much time and money and equipment is devoted to limiting the amount of normal tissue that is exposed to any radiation at all because the dose is high enough to cause toxicity.

This factor is important when considering treating cancers that are disseminated or have metastasized. In these cases, the nanoparticles labeled with antibodies or markers specific to the cancer cells will bind to the cells wherever they exist, even if that is outside the primary region of tumor. Since the approach disclosed herein is essentially nontoxic to non-cancerous cells, the radiation field can be enlarged to encompass cancer cells wherever they might be as determined by diagnostic imaging or by clinical judgment. This would not be possible when using conventional radiation where there is inverse relationship between the amount of dose one can deliver and the size of the region to which that dose is delivered.

In addition, since only cancer cells would be labeled, or would be labeled preferentially, with nanoparticles by the means described herein, and only cells that are so labeled will experience dose enhancement, non-cancerous cells lying within a tumor or target volume will be spared the most toxic effects of the radiation and may survive treatment.

Calibration and Monitoring of Therapy with Treatment Beams

Figure 35A:
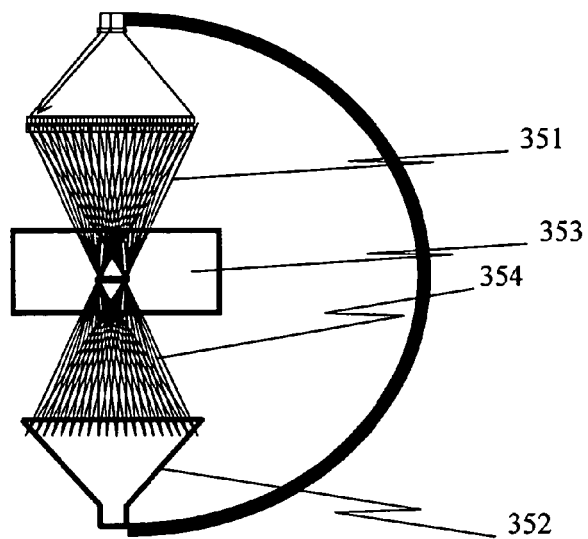
FIG. 35A, FIG. 35B and FIG. 35C shows using treatment beam to image patient and target.
Figure 35B:
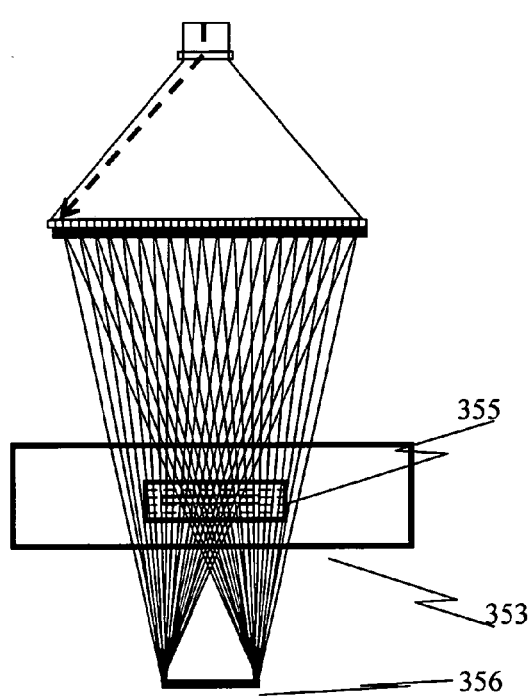
Figure 35C:
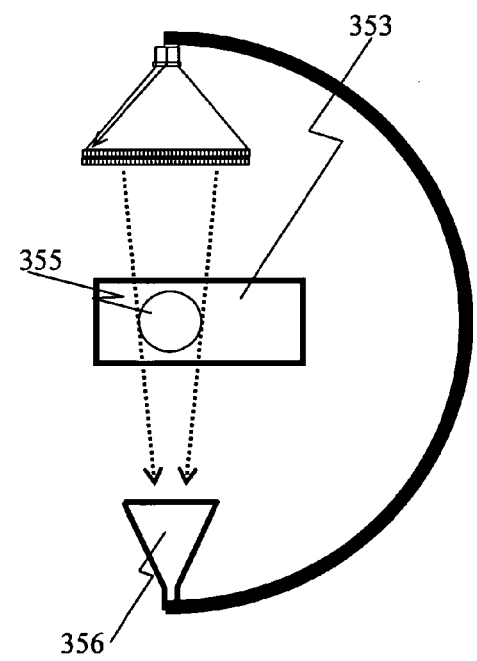

As mentioned previously, one of the factors determining the amount of dose enhancement is the concentration of Z material in the target. This can be assessed by using the array of beams used to deliver the treatment dose to also image the target volume. An x-ray detector 352 can be positioned 180 degrees opposite the beam array 351 in order to capture the radiation 354 as it diverges after exiting the patient 353 in FIG. 35A. Alternatively the radiation could actually be focused on the detector 355 in FIG. 35B with an appropriate choice of energy used to deposit maximum dose at the target region 355 in patient 353 as in FIG. 35B-FIG. 35C. The imaging characteristics of the target region as traversed by the array of beams can be determined prior to and following loading of the target with the Z material. Once a calibration curve is created relating concentration to change in imaging characteristics, this curve can be used to determine the concentration of Z material in the target volume. This concentration can then be used by a planning system to determine the appropriate values to be used for planning variables such that the desired dose can be delivered to the target region. The same detector can be used to localize the patient and to determine if the patient has moved by comparing imaging characteristics prior to and during treatment using the methods and means presented previously.

This combined approach may allow most tumors to be treated in a single fraction or very few fractions without risking damage to normal tissue. As mentioned it will also allow a serial radiosurgical treatment to be implemented whereby large single fraction doses are delivered repeatedly over time in order to kill cancer cells as they become oxygenated and therefore active. It will also do so in a very cost-effective manner. Unlike complex IMRT and IGRT capable megavoltage delivery devices that range in price from $3 M to in excess of $4 M depending on features, that require specially constructed rooms that may cost in excess of an additional $1 M to build, and that are quite time consuming when it comes to the planning and delivery of the treatment dose, low energy devices are low cost, easy to build, and can be made very compact. Unlike other low energy radiation devices that have been proposed for use, this invention will deliver the dose of radiation required to benefit from dose enhancement at a reasonable cost and in a reasonable amount of time regardless of the size or depth of the target region. The use of low energy reduces the need for user and patient shielding, making the device installable in almost any environment, increasing safety and reducing significantly the cost of building a treatment facility.

Other Variations

Each of the planning, localization, guidance, and monitoring features described herein can be applied to the convergent approach utilizing dose enhancement. In addition, many variations of the invention will occur to those skilled in the art. All such variations are intended to be within the scope and spirit of the invention. For instance:

(a) Multiple delivery units could be affixed to a C-arm device in order to improve efficiency of treatment delivery, or one head can be used for imaging, with a focal point outside the patient, and another for treatment with a focal point inside the patient.

(b) A variation for delivering the 2-D array of beams required for the convergent therapy would be to use a rotational support structure generating a 1-D array of beams that not only can rotate around a patient but also can angle its plane of rotation along an arc perpendicular to the initial plane of rotation. In this manner the rotational support would be indexed orthogonal to the plane of rotation between repeated rotations, thereby reproducing the 2-D array. That is, after the rotational tool has positioned the 1-D array in a plurality of positions around the patient along a single rotation around the patient, the rotational device is rotated perpendicular to the prior plan of rotation by an amount sufficient to reposition the array in the correct increment, thereby creating a new arc about which to rotate the device. By repeating this process many times, it is possible to create an effective 2-D array of beams delivered to the patient from a plurality of positions about the patient.

(c) The anode plate used in the scanning electron beam system can contain any number of targets all of which are not required to be activated in the course of a scan. For instance, assuming a 50 cm×50 cm plate containing 200×200 targets, in some applications all targets will be scanned whereas in some cases alternating rows will be scanned such that only 100× 100 targets are used creating an effective 2× spacing between the beams. Alternatively, an area of the plate only 10 cm×10 cm will be used. In each instance a different beam overlap geometry will be created resulting in a different and unique set of depth dose curves that can be tailored for the clinical condition to be treated.

Although some embodiments are shown to include certain features, the applicant(s) specifically contemplate that any feature disclosed herein may be used together or in combination with any other feature on any embodiment of the invention. It is also contemplated that any feature may be specifically excluded from any embodiment of an invention.

What is claimed is:

1. An apparatus for performing radiation therapy on a selected region of a tissue in proximity to said apparatus, said apparatus comprising:
    a radiation source for generating a plurality of beams of radiation;
    a positioner for disposing said plurality of beams in a predetermined and controllable manner from a plurality of linear positions indexed relative to each other in predetermined increments so as to produce an array of said plurality of beams that overlap in increasing amounts as said plurality of beams pass through said tissue, whereby an amount of radiation delivered at depth in said tissue is equal to or greater than a dose delivered to a tissue surface through which the plurality of beams pass; and
    a treatment planner for creating a treatment plan wherein said treatment plan comprises said amount of radiation delivered to said depth and a location of said depth and wherein said treatment planner is configured to communicate said treatment plan to said positioner.

2. The apparatus of claim 1 further comprising:
    an imaging device for imaging markers placed on a patient;
    a detector for detecting a difference in a position of said markers between two different points of time, and
    whereby said treatment plan can be adjusted automatically to compensate for detected movement.

3. The apparatus of claim 1 further comprising:
    an attenuator for attenuating said plurality of beams to harden said plurality of beams.

4. The apparatus of claim 1 further comprising:
    a movement detector for detecting movement of said tissue during said therapy and modifying said therapy based on said detected movement.

5. The apparatus of claim 4 further comprising:
    a tracking system for tracking position of markers placed on said tissue.

6. The apparatus of claim 1 wherein said plurality of beams are converging beams.

7. The apparatus of claim 1 wherein said plurality of beams are diverging beams.

8. The apparatus of claim 1 wherein said array is a one dimensional array.

9. The apparatus of claim 1 wherein said array is a two dimensional array.

10. The apparatus of claim 1 wherein said plurality of beams are x-ray beams with energy of at least 20 kVp.

11. The apparatus of claim 10 further comprising:
    a scanning electron beam device.

12. An apparatus for performing radiation therapy on a selected region of a tissue in a patient, said apparatus comprising:
    a radiation therapy source for generating a plurality of beams of radiation;
    a positioner for positioning said plurality of beams in a predetermined and controllable manner from a plurality of linear positions indexed relative to each other in predetermined increments so as to produce an array of said plurality of beams that overlap in said tissue,
    whereby an amount of radiation delivered to the region is increased relative to a dose delivered to a tissue surface through which the beams pass; and
    an imaging device for determining a target location and effects of treatment.

13. The apparatus of claim 12 wherein said plurality of beams are x-ray beams with energy of at least 20 kVp.

14. The apparatus of claim 13 further comprising:
    a scanning electron beam device.

15. The apparatus of claim 12 further comprising:
    a treatment planner for creating a treatment plan wherein said treatment plan comprises said amount of radiation delivered to said region and a location of said region.

16. A method for performing radiation therapy to a region of tissue in a patient comprising:
    positioning a beam of radiation to generate a plurality of beams of radiation indexed relative to each other in predetermined increments;
    creating a linear array of overlapping beams that converge at a specified depth; and
    increasing a therapy dose of radiation delivered at said depth relative to a dose delivered to other tissue at tissue surface.

17. The method of claim 16 further comprising:
    generating a treatment plan comprising said dose of radiation delivered to said depth and a location of said depth.

18. The method of claim 16 further comprising:
creating a second linear array of overlapping beams that converge at said specified depth.

19. The method of claim 16 wherein said beam of radiation is an x-ray beam with energy of at least 20 kVp.

20. The method of claim 19 further comprising:
scanning an electron beam over an anode target.

* * * * *